(12) United States Patent
Croxford et al.

(10) Patent No.: US 12,265,603 B2
(45) Date of Patent: Apr. 1, 2025

(54) ELECTRONIC AUTHENTICATION SYSTEM, DEVICE AND PROCESS

(71) Applicant: Arm Limited, Cambridge (GB)

(72) Inventors: Daren Croxford, Swaffham Prior (GB); Roberto Lopez Mendez, Cambridge (GB); Mbou Eyole, Soham (GB); Matthew James Horsnell, Cambridge (GB)

(73) Assignee: Arm Limited, Cambridge (GB)

( * ) Notice: Subject to any disclaimer, the term of this patent is extended or adjusted under 35 U.S.C. 154(b) by 485 days.

(21) Appl. No.: 17/429,222

(22) PCT Filed: Jul. 26, 2019

(86) PCT No.: PCT/GB2019/052097
§ 371 (c)(1),
(2) Date: Aug. 6, 2021

(87) PCT Pub. No.: WO2020/161456
PCT Pub. Date: Aug. 13, 2020

(65) Prior Publication Data
US 2022/0129534 A1    Apr. 28, 2022

Related U.S. Application Data

(63) Continuation of application No. 16/271,760, filed on Feb. 8, 2019, now Pat. No. 11,803,627.

(51) Int. Cl.
*G06F 21/00* (2013.01)
*A61B 5/00* (2006.01)
(Continued)

(52) U.S. Cl.
CPC ............ *G06F 21/36* (2013.01); *A61B 5/0053* (2013.01); *A61B 5/117* (2013.01); *A61B 5/378* (2021.01); *A61B 5/38* (2021.01); *A61B 5/7264* (2013.01)

(58) Field of Classification Search
None
See application file for complete search history.

(56) References Cited

U.S. PATENT DOCUMENTS

| | | | |
|---|---|---|---|
| 2009/0063866 A1* | 3/2009 | Navratil | A61B 5/377 706/47 |
| 2016/0103487 A1* | 4/2016 | Crawford | A61B 5/117 600/544 |

(Continued)

FOREIGN PATENT DOCUMENTS

WO    2017201972 A1    11/2017

OTHER PUBLICATIONS

Application, U.S. Appl. No. 16/271,760, filed Feb. 8, 2019, 101 Pages.

(Continued)

*Primary Examiner* — Andrew J Steinle
(74) *Attorney, Agent, or Firm* — Berkeley Law & Technology Group, LLP

(57) ABSTRACT

Briefly, example methods, apparatuses, and/or articles of manufacture are disclosed that may be implemented, in whole or in part, using one or more processing devices to facilitate and/or support one or more operations and/or techniques for authenticating an identity of a subject. In particular, some embodiments are directed to techniques for authentication of an identity of a subject as being an identity of a particular unique individual based, at least in part, on involuntary responses by the subject to sensory stimuli.

19 Claims, 10 Drawing Sheets

(51) Int. Cl.
*A61B 5/117* (2016.01)
*A61B 5/378* (2021.01)
*A61B 5/38* (2021.01)
*G06F 21/36* (2013.01)

(56) References Cited

U.S. PATENT DOCUMENTS

2017/0228526 A1    8/2017   Cudak et al.
2017/0346817 A1   11/2017   Gordon et al.
2018/0012009 A1*   1/2018   Furman .................. G06N 3/088

OTHER PUBLICATIONS

Filing Receipt, U.S. Appl. No. 16/271,760, Mailed Feb. 28, 2019, 3 Pages.
Notice of Publication, U.S. Appl. No. 16/271,760, Mailed Aug. 13, 2020, 1 Page.
Schalk, et al, "Brain Sensors and Signals," A Practical Guide to Brain-Computer Interfacing with BC12000, http://www.springer.com/978-1-84996-091-5, 2010, pp. 9-35.
Cecotti, et al, "Convolutional Neural Networks for P300 Detection with Application to Brain-Computer Interfaces," IEEE Transactions on Pattern Analysis and Machine Intelligence, vol. 33, No. 3, Mar. 2011, pp. 433-445.
Malmivuo, et al, "Principles and Applications of Bioelectric and Biomagnetic Fields," www.biolabor.hu, Jan. 1995, pp. 364-374.
Kus, et al, "On the Quantification of SSVEP Frequency Responses in Human EEG in Realistic BCI Conditions," PLOS ONE, vol. 8, Issue 10, e77536, www.plosone.org, Oct. 2013, 9 Pages.
Kha, et al, "Real-Time Brainwave-Controlled Interface Using P300 Component in EEG Signal Processing," The 2016 IEEE RIVF International Conference on Computing & Communication Technologies, Research, Innovation, and Vision of the Future, IEEE, 978-1-5090-4134-3/16, 2016, pp. 235-240.
Notification of Transmittal of the International Search Report and the Written Opinion of the International Searching Authority, or the Declaration, App. No. PCT/GB2019/052097, Mailed Oct. 28, 2019, 1 Page.
International Search Report, App. No. PCT/GB2019/052097, Mailed Oct. 28, 2019, 4 Pages.
Written Opinion of the International Searching Authority, App. No. PCT/GB2019/052097, Mailed Oct. 28, 2019, 9 Pages.
Notification Concerning Transmittal of International Preliminary Report on Patentability and Written Opinion of the International Searching Authority, App. No. PCT/GB2019/052097, Mailed Aug. 19, 2021, 9 Pages.
Das, et al, "EEG Biometrics Using Visual Stimuli: A Longitudinal Study," IEEE Signal Processing Letters, vol. 23, No. 3, Mar. 2016, 5 pages.
Gui, et al, "Exploring EEG-based Biometrics for User Identification and Authentication," 2014 IEEE Signal Processing in Medicine and Biology Symposium (SPMB), DOI: 10.1109/SPMB.2014.7002950, Dec. 13, 2014, 6 pages.
Wired UK, "Biometrics: 'Brainprint' can identify individuals with 100 per cent accuracy," https://www.wired.com/story/eeg-brainprint-biometric-identification/, downloaded Apr. 4, 2019, 16 pages.
Švogor, et al, "Two factor authentication using EEG augmented passwords," https://ieeexplore.ieee.org/abstract/document/6308035, Jun. 25-28, 2012, 6 pages.
XRDC, "AR/VR Innovation Report Aug. 2018," xrdconf.com, https://duckduckgo.com/?q=AR%2FVR+Innovation+Report+Aug.2018+site%3Aartillry.co&atb=v262-1&ia=web, Presented Oct. 29-30, 2018, 60 pages.
Neurosky, "Enhancing AR/VR Devices with EEG and ECG Biosensors," https://neurosky.com/2018/01/enhancing-arvr-devices-with-eeg-and-ecg-biosensors/, Jan. 29, 2018, downloaded Apr. 4, 2019, 6 pages.
Neurosky, "Introductory Guide to EEG & BCI for Entertainment," https://www.neurosky.com/wp-content/uploads/2016/06/Intro-Guide-EEG-BCI.pdf, copy right 2015, 11 pages.
Office Action, U.S. Appl. No. 16/271,760, Mailed Jun. 30, 2022, 22 pages.
Response to Office Action, U.S. Appl. No. 16/271,760, filed Sep. 22, 2022, 18 pages.
Final Office Action, U.S. Appl. No. 16/271,760, Mailed Feb. 9, 2023, 12 pages.
Response to Final Office Action, U.S. Appl. No. 16/271,760, filed Apr. 4, 2023, 16 pages.
Advisory Action, U.S. Appl. No. 16/271,760, Mailed Apr. 20, 2023, 4 pages.
RCE, U.S. Appl. No. 16/271,760, filed May 9, 2023, 20 pages.
Notice of Allowance, U.S. Appl. No. 16/271,760, Mailed Jun. 27, 2023, 8 pages.
Issue Fee, U.S. Appl. No. 16/271,760, filed Sep. 25, 2023, 5 pages.
Issue Notification, U.S. Appl. No. 16/271,760, Mailed Oct. 11, 2023, 2 pages.
Office Action, App. No. CN201980091468.7, Mailed Nov. 7, 2024, 31 pages.
Response to Office Action, App. No. CN201980091468.7, Filed Dec. 10, 2024, 60 pages.

* cited by examiner

US 12,265,603 B2

1

ELECTRONIC AUTHENTICATION SYSTEM, DEVICE AND PROCESS

This International Application claims the benefit of and priority to U.S. Non-provisional patent application Ser. No. 16/271,760, entitled "AUTHENTICATION SYSTEM, DEVICE AND PROCESS," filed on 8 Feb. 2019 which is, in its entirety, incorporated herein by reference.

The present disclosure relates generally to electronic authentication processes.

Modern security processes typically employ authentication techniques to verify or confirm an identity of a subject (e.g., user) as a precondition for secure access to a computing system. Disadvantages of requiring users to remember multiple passwords (which are often many characters long) are well known. Other techniques to authenticate users as a precondition for secure access to a computing system are typically cumbersome and detract from a user experience.

Claimed subject matter is particularly pointed out and distinctly claimed in the concluding portion of the specification. However, both as to organization and/or method of operation, together with objects, features, and/or advantages thereof, it may best be understood by reference to the following detailed description if read with the accompanying drawings in which:

Figure 1:
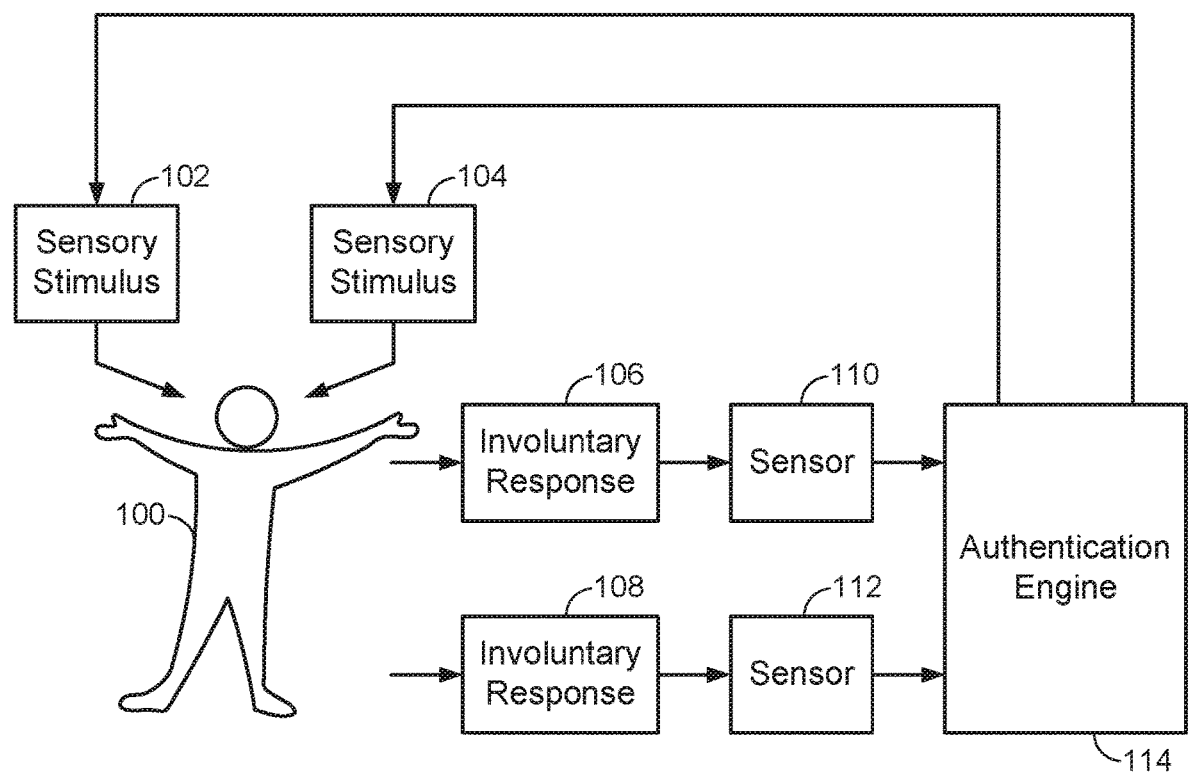
FIG. 1 is a schematic diagram of an example system to electronically authenticate an identity of a subject according to embodiments.

Reference is made in the following detailed description to accompanying drawings, which form a part hereof, wherein like numerals may designate like parts throughout that are corresponding and/or analogous. It will be appreciated that the figures have not necessarily been drawn to scale, such as for simplicity and/or clarity of illustration. For example, dimensions of some aspects may be exaggerated relative to others. Further, it is to be understood that other embodiments may be utilized. Furthermore, structural and/or other changes may be made without departing from claimed subject matter. References throughout this specification to "claimed subject matter" refer to subject matter intended to be covered by one or more claims, or any portion thereof, and are not necessarily intended to refer to a complete claim set, to a particular combination of claim sets (e.g., method claims, apparatus claims, etc.), or to a particular claim. It should also be noted that directions and/or references, for example, such as up, down, top, bottom, and so on, may be used to facilitate discussion of drawings and are not intended to restrict application of claimed subject matter. Therefore, the following detailed description is not to be taken to limit claimed subject matter and/or equivalents.

References throughout this specification to one implementation, an implementation, one embodiment, an embodiment, and/or the like means that a particular feature, structure, characteristic, and/or the like described in relation to a particular implementation and/or embodiment is included in at least one implementation and/or embodiment of claimed subject matter. Thus, appearances of such phrases, for example, in various places throughout this specification are not necessarily intended to refer to the same implementation and/or embodiment or to any one particular implementation and/or embodiment. Furthermore, it is to be understood that particular features, structures, characteristics, and/or the like described are capable of being combined in various ways in one or more implementations and/or embodiments and, therefore, are within intended claim scope. In general, of course, as has always been the case for the specification of a patent application, these and other issues have a potential to vary in a particular context of usage. In other words, throughout the disclosure, particular context of description and/or usage provides helpful guidance regarding reasonable inferences to be drawn; however, likewise, "in this context" in general without further qualification refers at least to the context of the present patent application.

As more advanced forms of interaction between humans and computers emerge, one or more signals obtained from one or more sensors generated responsive to one or more involuntary actions of a human subject (e.g., user), for example, may enable certain enhanced computing services. For example, in some instances, sensor signals may exhibit a unique "signature" by being indicative of or responsive to certain bodily processes of a human (e.g., involuntary processes). According to an embodiment, a process to authenticate an identity of a human subject may comprise, for example, applying one or more sensory stimuli to the human subject and evaluating one or more corresponding involuntary responses by the human subject (e.g., as monitored from sensor signals).

In this context, an "involuntary response" as referred to herein means an action and/or phenomenon generated by a subject (e.g., human subject) responsive to a presence of a stimulus wherein generation of the action and/or phenomenon is not under conscious control by the subject. As an example, one particular involuntary response by a human subject to sensory stimuli may include brain signals. By way of example, electroencephalography (EEG) is a non-invasive technique of detecting, processing and/or recording brain signals including brain signals generated responsive to sensory stimuli. Human brain signals may be generated by electrical activity in a brain as neurons exchange signals. If a sufficient number of neurons fire simultaneously, electrical patterns associated with a specific region of a brain may be sensed by electrodes placed on or close to a scalp and associated circuitry in proximity to such electrodes. While a spatial resolution of EEG signals may be relatively coarse, EEG signals may be temporally resolved to a sufficient degree after suitable signal amplification and filtering for use in determining command and control signals for a human-computer interface.

FIG. 1 is a schematic diagram of an example operating environment to authenticate an identity of a human subject 100 based, at least in part, on one or more involuntary responses such as, for example, 106 and/or 108 to sensory stimuli 102 and/or 104 according to embodiments. In a particular implementation, an operating environment may include authentication engine 114, which may comprise, for example, one or more computing devices capable of executing device-readable instructions, such as executable instructions stored in a non-transitory medium to generate signals initiating sensory stimuli 102 and/or 104, and process signals from sensors 110 and/or 112 indicative of involuntary responses (e.g., involuntary responses 106 and/or 108) from human subject 100 to sensory stimuli 102 and/or 104.

Thus, according to an embodiment, sensors 110 and/or 112 may generate voltage and/or current signals, such as voltage and/or current signals generated responsive to and/or indicative of involuntary responses 106 and/or 108. In some examples, these or like voltage and/or current signals may be amplified, filtered, sampled, correlated and/or otherwise processed to provide a digital signal to be further processed by authentication engine 114 (e.g., by execution of device-readable instructions on a processor), for example.

In a particular implementation, sensors 110 and/or 112 may be integrated as part of a brain computer interface (BCI) to detect and/or measure involuntary responses 106 and/or 108 as brain signals. Particular features of an example BCI are described herein, such as with reference to FIG. 2A, for example. Optionally or alternatively, sensors 110 and/or 112 may comprise, for example, wearable electrodes communicatively coupled to (e.g., located by) muscles in the heart and/or around the lungs, or other appropriate portions of the body of human subject 100. In another alternative implementation, sensors 110 and/or 112 may comprise, for example, sensors capable of detecting eye blinking (e.g., for monitoring a frequency of eye blinking), sensors capable of tracking directional movement of eyes, sensors capable of detecting and/or measuring a pupillary response, sensors capable of measuring small magnetic fields produced in a brain (e.g., to perform a magnetoencephalography (MEG) scan), sensors capable of measuring changes in body temperature, changes in electrical impedance or perspiration, just to provide a few additional examples of involuntary responses detectable by sensors. It should be understood, however, that these are merely examples of sensors that are capable of responding to an involuntary response by a human subject (e.g., by generating a voltage and/or current signal), and that claimed subject matter is not limited in this respect.

According to an embodiment, sensory stimulus 102 may be associated with an identity of human subject 100, for example and may evoke a corresponding detectable or measurable involuntary response in human subject 100. In other words, sensory stimulus 102 may be selected to evoke a particular involuntary response in a particular unique individual that would not likely be evoked in another, different human subject. In an implementation, sensory stimulus 102 may be generated from a particular electronic file stored in memory or like repository, such as an electronic library that may be selected from and/or uniquely associated with a particular unique individual. In one particular application, a bank or other like financial organization may maintain a library of electronic documents including, for example, electric documents associated with identities of clients. For example, a particular electronic document maintained in a library may be used, at least in part, to generate one or more sensory stimuli to evoke a particular involuntary response in a particular unique client associated with such a particular electronic document maintained in a library, but not evoke such a particular involuntary response in a human subject other than such a particular unique client. In other words, a sensory stimulus generated based, at least in part, on an electronic document, if applied to such a particular unique client, may evoke a particular involuntary response in the particular unique client, for example, and may not likely evoke such a particular involuntary response if applied to a human subject other than the particular unique client. Other types of organizations and/or systems may similarly maintain a library of electronic files associated with particular unique individuals for use in electronically authenticating identities of human subjects as being identities of particular unique individuals, for example, and claimed subject matter is not limited in this respect. In other implementations, specific computing devices and/or platforms, such as gaming/virtual reality platforms or electronic equipment where fingerprint scan may be cumbersome and/or impractical (e.g., in a laboratory, factory or office), may similarly maintain a library of electronic files associated with particular unique individuals for use in electronically authenticating identities of subjects as being identities of the particular unique individuals (e.g., as a precondition for access).

Depending on an implementation, sensory stimulus 102 may comprise, for example, one or more visual images (e.g., visual image sequences), audible sounds (e.g., speech), a haptic stimulus (e.g., application of light pressure or vibrations to various locations of a scalp of human subject 100), just to provide a few examples of sensory stimuli that may evoke a corresponding detectable or measurable involuntary response in a human subject.

In one implementation, sensory stimulus 102 may be provided in a series or stream of sensory stimuli, for example, wherein sensory stimulus 102 (e.g., evoking a particular involuntary response in a particular unique individual that may not be evoked generally in another human subjects) may be temporally interleaved with sensory stimuli that may evoke an involuntary response generally in human subjects (e.g., portions of sensory stimuli that may evoke an involuntary response generally in a human subject may be insert between durational segments of sensory stimulus 102). Here, involuntary response 106 may be detected to be temporally correlated with application of sensory stimulus 102 to human subject 100. For example, if sensory stimulus 102 is selected to evoke a corresponding involuntary response in a particular unique individual (e.g., and not just any individual human being), involuntary response 106 occurring at a particular time relative to a time of application of stimulus 102 may indicate that human subject 100 may indeed be the particular unique individual. In at least one example implementation, application of sensory stimulus 102 may, for example, evoke a so-called "P300 brain signal" in human subject 100. Here, such a P300 brain signal may comprise, as measured in an EEG signal for example, a deflection in a voltage with a particular latency (e.g., delay between stimulus and response) of roughly 250 to 500 ms. In some instances, a P300 brain signal detectable in a human subject may be evoked responsive, at least in part, to cognitive functioning in a brain of such a human subject, such as occurring responsive to a sensory stimulus experienced by such a human subject, for example. However, a P300 brain signal is merely an example a phenomenon that may be evoked in a human subject responsive at least in part to cognitive functioning in a brain, and involuntary response 106 may comprise other phenomena such as, for example, phenomena detectable by a MEG scan, eye movement, pupillary response, heartbeat, etc. that may be used individually and/or in combination to detect a response to cognitive function by the human subject. In an implementation, and as discussed in greater detail herein, sensory stimulus 102 may be temporally interleaved with other sensory stimuli not expected to evoke P300 brain signal (or other phenomenon evoked responsive at least in part to cognitive functioning in a brain), thus, facilitating and/or supporting detection of a P300 brain signal in involuntary response 106 according to a so-called "odd ball" paradigm, as discussed herein.

According to an embodiment, sensory stimulus 104 may comprise, for example, a stimulus that may likely evoke a predetermined involuntary response 108, such as temporally correlated with sensory stimulus 102 and involuntary response 106 (e.g., evoked by application of sensory stimulus 102, etc.). In an implementation, involuntary response 108 may, for example, occur independently of application of sensory stimulus 102, and therefore may occur in a presence or absence of involuntary response 106. Also, involuntary response 108 may occur at an expected time lag preceding or following application of sensory stimulus 104, for example, and, in some instances, involuntary response 106 may be expected to occur at a set or predetermined time prior to or following detection of involuntary response 108. Furthermore, application of sensory stimulus 104 may evoke a detectable and/or measurable response (e.g., involuntary response 108) generally in multiple different human subjects, not limited to a particular unique individual. In other words, in some instances, sensory stimulus 104 applied to multiple different human subjects may evoke a similar or like detectable involuntary response 108 in such multiple different subjects at an expected time lag preceding or following application of sensory stimulus 104.

According to an embodiment, sensory stimulus 104 as applied to human subject 100 may be temporally correlated with sensory stimulus 102. For example, sensory stimulus 104 may be applied at a particular instance relative to application of sensor stimulus 102, such as at a set (e.g., predetermined) time preceding or following application of sensory stimulus 102. In a process to authenticate an identity of human subject 100 as being an identity of a particular unique individual, involuntary response 108 (which may be temporally correlated with involuntary response 106) may be used to confirm that a response detected as involuntary response 106 in fact occurs responsive to a sensory stimulus 102 (that is to evoke involuntary response 106 in such a particular unique individual). In an embodiment, a candidate detection of involuntary response 106 may, for example, be confirmed, such as via authentication engine 114, for example, as being from a particular unique individual if a corresponding detection of an involuntary response 108 temporally correlates with such a candidate detection of involuntary response 106. This may, for example, reduce or eliminate incidences of false positive authentication of an identity of a human subjects as being that of particular unique individuals of interest.

According to an embodiment, if an involuntary response 106 (e.g., evoked in a particular unique individual) is expected, an expected time lag or difference between a time of detection ($t_1$) of an involuntary response 106 and a time of detection ($t_2$) of a temporally correlated involuntary response 108 may be expressed as $\Delta$. Here, if an involuntary response 106 is expected to lead a temporally correlated involuntary response 108 by a duration $\Delta$, for example, detection of an event at time $t_e$ may be confirmed as a detection of an involuntary response 106 responsive to a condition at expression (1) as follows:

$$\Delta - \in < t_2 - t_e < \Delta + \in, \quad (1)$$

Where $\in$ denotes an error term.

If, on the other hand, an involuntary response 106 is expected to lag a temporally correlated involuntary response 108 by a duration $\Delta$, for example, detection of an event at time $t_e$ may be confirmed as a detection of an involuntary response 106 responsive to a condition at expression (2) as follows:

$$\Delta - \in < t_e - t_2 < \Delta + \in. \quad (2)$$

According to an embodiment, detection of involuntary responses occurring at times $t_1$ and $t_2$ may, for example, be performed responsive to detection of particular sensor characteristics (e.g., detection of particular signal characteristics in signals generated by sensors 110 and/or 112). For example, a time $t_e$ and/or $t_2$ may be determined based, at least in part, on detection of particular voltage and/or current signals generated by sensor 110 and/or 112 (e.g., detection of a voltage peak, etc.). In one particular implementation as discussed below, a time $t_2$ may, for example, be determined based, at least in part, on a detected occurrence of a frequency characteristic and/or amplitude variation in a signal generated by sensor 112.

According to an embodiment, a time between initiation of sensory stimulus 102 and occurrence of detection of involuntary response 106 may vary from human being to human being due, at least in part, to individual-specific physiology. Likewise, a time between initiation of sensory stimulus 104 and occurrence of detection of involuntary response 108 may similarly vary from human being to human being due, at least in part, to individual-specific physiology. As such, a value for $\Delta$ discussed above in connection with expressions (1) and (2) may vary from human being to human being due, at least in part, to individual-specific physiology. While sensory stimulus 102 may be selected/determined to evoke involuntary response 106 in a particular unique individual, in application of expressions (1) or (2), for example, a particular value for $\Delta$ may be selected and/or determined based, at least in part, on physiology specific to such a particular unique individual. For example, in applying expression (1) or (2) a value of $\Delta$ for a particular unique individual may be selected and/or determined based, at least in part, on one or more prior observations of involuntary responses by such a particular unique individual to appropriate sensory stimuli.

Figure 2A:
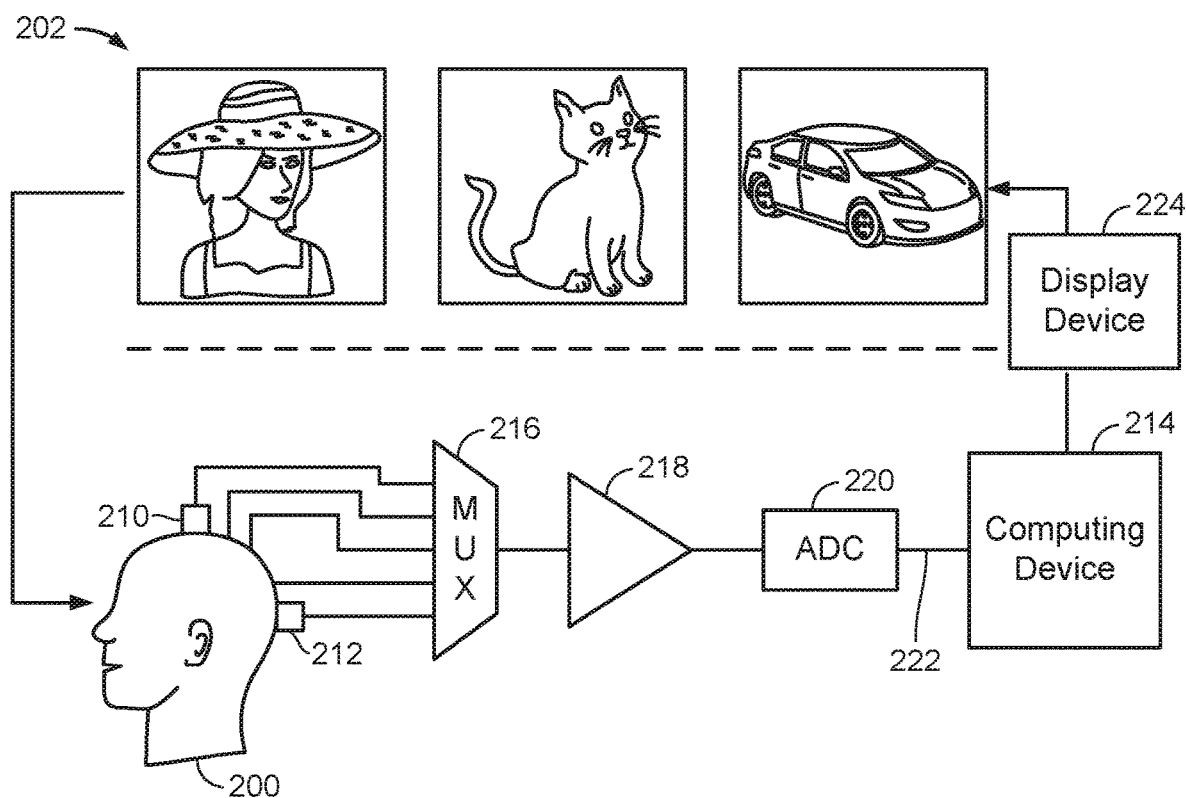
FIG. 2A is a schematic diagram of an example system to authenticate an identity of a subject according to particular embodiments.

FIG. 2A is a schematic diagram of an example system to electronically authenticate a human subject according to one and/or more aspects or implementations of a system shown in FIG. 1. A sensory stimulus applied to human subject 200 may comprise presentation to human subject 200 of a series of visual images 202 in which one or more images are of particular significance to a particular unique individual (e.g., a particular individual who may or may not be the same as human subject 200). Presentation of the one or more images of particular significance to such a particular unique individual may further be temporally interleaved with presentation of random images that are of no particular significance to such a particular unique individual. Such an image of particular significance may comprise, for example, an image of something of personal significance to a particular unique individual such as a portrait of a family member, childhood scene or other image that potentially evokes an "attention grabbing" response (e.g., a response based, at least in part, on a cognitive reaction to stimuli of personal significance to a particular unique individual) in such a particular unique individual (but not generally in individuals other than the particular unique individual). In an embodiment of an authentication process, if presentation to human subject 200 of one or more images of particular significance evokes such an attention grabbing response (e.g., involuntary response) in human subject 200, it may be inferred that an identity of human subject 200 is an identity of such a particular unique individual.

According to an embodiment, a brain computer interface (BCI) may detect, process and/or characterize brain signals generated by human subject 200 in response to sensory stimuli. For example, sensors 210 and 212 may be positioned to be in contact with a scalp of human subject 200 to, among other things, generate voltage and/or current signals characterizing signals occurring in a brain of human subject 200 in response to sensory stimuli. Sensors 210 and 212 may comprise, for example, any one of several electrodes suitable for non-invasive placement on the scalp of human subject 200 to support electroencephalography (EEG) brain signal processing. In a particular implementation, sensors 210 and 212 may be attached to specific positions on a headset (not shown) to precisely position sensors 210 and 212 on specific locations of the scalp of human subject 200 (e.g., in contact with bare scalp and/or in close enough proximity in the presence of hair to receive and/or process brain signals). For example, sensors 210 and 212 may be integrated with a virtual reality (VR) headset, augmented reality (AR) headset including one or more audio speakers, a microphone and one or more display devices (e.g. implemented as display device 224) for displaying images. Similarly, sensors 210 and 212 may be integrated with an augmented reality (AR) headset and/or AR glasses. In alternative implementations, sensors 210 and 212 may comprise electrodes that are placed on the surface of a brain of human subject 200 to support electrocorticography (ECoG), or may comprise electrodes placed invasively within the brain of human subject 200 to support single-neuron recordings. It should be understood that these are merely examples of sensors that may be integrated as part of a BCI, and claimed subject matter is not limited in this respect.

A BCI to process voltage and/or current signals generated by sensors 210 and 212 may further include multiplexer (MUX) 216, buffer/amplifier 218 and analog-to-digital converter (ADC) 220. In an implementation, sensors 210 and 212, MUX 216, buffer/amplifier 218 and ADC 220 may be integrated in a headset adapted to be fitted to a scalp of human subject 200 for proper placement of sensors 210 and 212 in contact with particular locations of such a scalp of human subject 200. ADC 220 may be coupled to computing device 214 by a communication link 222 having suitable message signal throughput and low latency such as, for example, a wired communication link (e.g., Universal Serial Bus) or wireless communication link (e.g., Bluetooth® or version of IEEE std. 802.11), just to provide a few examples. In an embodiment, messages may be transmitted in signal packets or signal frames between ADC 220 and computing device 214, and may be encrypted to enhance security to avoid hacking of an authentication process, for example.

According to an embodiment, MUX 216 may comprise specialized processing hardware to assist in combining signals generated by multiple sensors including sensors 210 and 212. In one particular example, MUX 216 may comprise a machine-learning processor to assist in fusing, filtering and/or otherwise processing current and/or voltage signals generated by sensors 210 and 212, and classification of detected signal characteristics for use in additional processing. In one particular implementation, MUX 216 may be adapted to implement one or more techniques for detection and classification of P300 brain signals based, at least in part, on current and/or voltage signals generated by sensors 210 and 212 such as described in H. Cecotti and A. Graser "Convolutional Neural Networks for P300 Detection with Application to Brian-Computer Interfaces," IEEE Transactions on Pattern Analysis and Machine Intelligence, Vol. 33, No. 3, March 2011, or described in Ha Hoang Kha and Vo Anh Kha, "Real-Time Brainwave-Controlled Interface Using P300 Component in EEG Signal Processing," The 2016 IEEE RIVF International Conference on Computing & Communication Technologies, Research, Innovation, and Vision for the Future. In another particular implementation, MUX 216 may be configured to implement one or more techniques for detection and classification of steady-state visual evoked potential (SSVEP) signals based, at least in part, on current and/or voltage signals generated by sensors 210 and 212 such as described in Rafal Kus, Anna Duszyk, Piotr Milonowski, Maciej Labecki, Maria Bierzynska, Zofia Radzikowka, Magdalena Michalska, Jaroslaw Zygierewicz, Piotr Suffcznski and Piotr Jerzy Durka, "On the Quantification of SSVEP Frequency Responses in Human EEG in Realistic BCI Conditions," PLOS ONE, Volume 8, Issue 10, October 2013. MUX 216 may also perform other signal processing and conditioning operations including, for example and without limitation, adjustments of bias and/or dynamic range of signals. It should be understood, however, that these are merely examples of how MUX 216 may be adapted to process current and/or voltage signals generated by sensors 210 and 212, and that claimed subject matter is not limited in this respect.

According to an embodiment, computing device 214 may control presentation of visual images 202 for viewing by human subject 200 through display device 224 such as, for example, an LED display device, LCD display device, OLED display device and/or a projector. As discussed herein, display device 224 may be positioned over eyes of human subject 200 and integrated as part of a VR and/or AR headset including speakers, microphone and sensors 210 and 212 positioned for placement at specific locations of a scalp of human subject 200. In one implementation, computing device 214 may control timing of a sequence of presentation of visual images 202 through display device 224 according to a time reference such as a time reference to a clock signal. In an embodiment, a BCI formed by sensors 210 and 212, MUX 216, buffer/amplifier 218 and ADC 220 may apply "time stamps" to observations of brain signals detected at sensors 210 and 212. These time stamps may be referenced to a time reference that is maintained by computing device 214 and that is used in controlling timing of a sequence of presentation of visual images 202.

An image of significance to a particular unique individual in or among visual images 202 may evoke a so-called "P300" brain signal in human subject 200 (e.g., if human subject 200 happens to in fact be such a particular unique individual), which may comprise a detectable brain signal that is produced at a particular delay (e.g., at a delay of about 300 ms depending on a particular physiology of human subject 200) after application of interesting (e.g., attention-grabbing) but unexpected sensory stimulus such as a visual image. Detection of such a P300 brain signal may rely on the aforementioned "odd-ball" paradigm in which presentations of sequences of repetitive stimuli are infrequently interrupted by a deviant stimulus. In this case, a deviant stimulus may comprise a visual image of significance to a particular unique individual among other images of no particular significance to such a particular unique individual. A reaction of human subject 200 to such an "oddball" stimulus may be recorded. In a particular implementation, sensors, such as sensors 210 and 212, may be attached to a scalp of human subject 200 to detect a P300 brain signal generated by human subject 200 responsive to such an oddball stimulus.

Figure 2B:
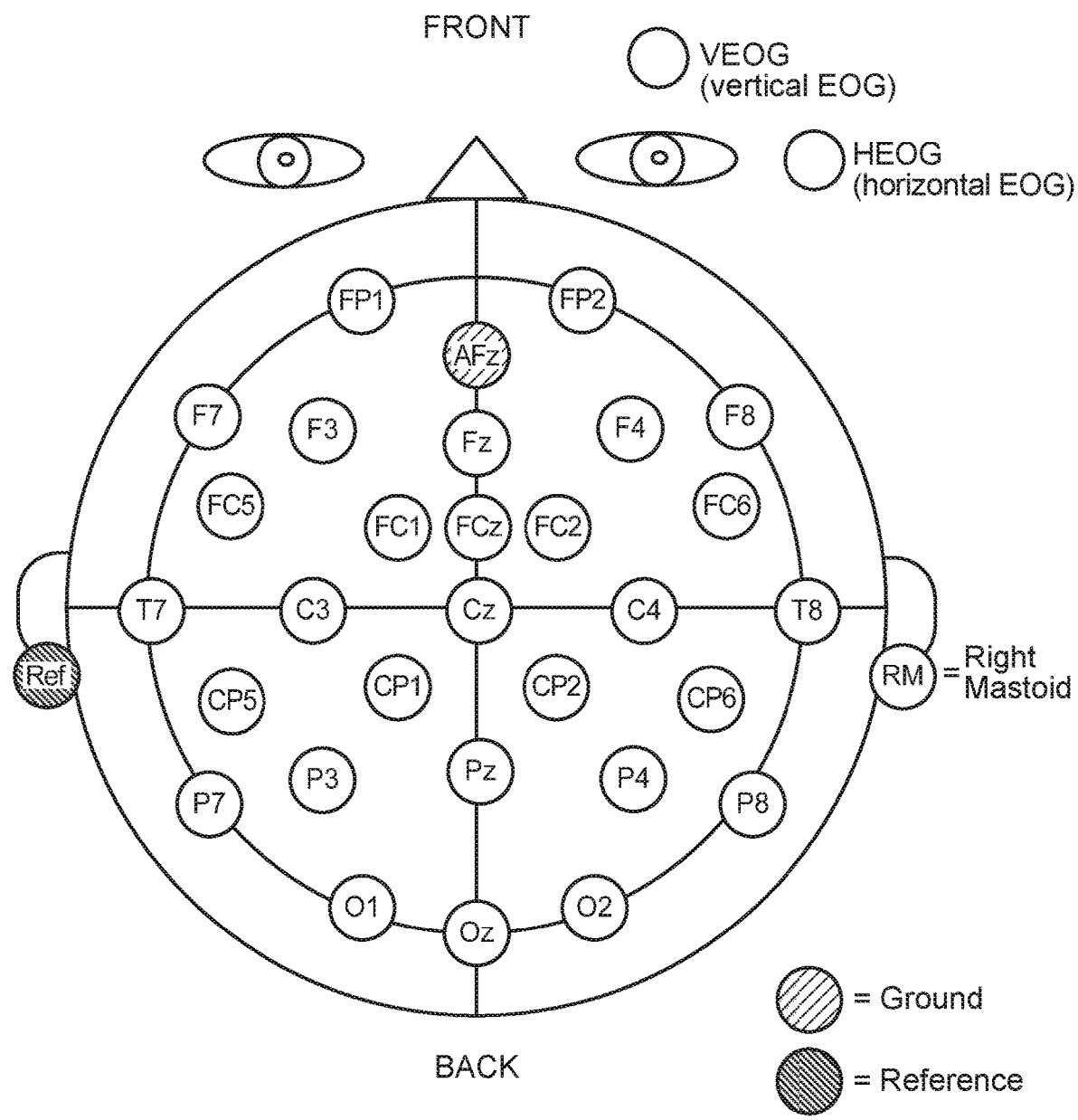
FIG. 2B is a schematic diagram illustrating possible example locations on a human scalp for positioning sensors for brain signal detection according to particular embodiments.

Exact placement of sensors on locations of a human scalp for effective detection of brain signals may vary between and/or among human subjects. FIG. 2B is a schematic diagram illustrating possible placement of sensors on a scalp of a human subject (e.g., placement of sensors 210 and 212 integrated in a VR headset on locations of a scalp of human subject 200). Those skilled in the art may recognize that sensors may be positioned on locations of a scalp of a human subject according to a scheme such as the international 10-20 system, describing suitable locations on a scalp for a range of purposes such as described in J. Malmivuo and R. Plonsey, *Bioelectromagnetism: Principles and Applications of Bioelectric and Biomagnetic Fields*, 1995, pp. 364-374. Locations on a scalp for placement of sensors may be selected based, at least in part, on proximity to certain brain regions of interest. In the particular implementation of FIG. 2B, for example, positions for favorable P300 brain signal detection in one embodiment may include F3, F4, FC5, FC6, P7 and P8. In other embodiments, sensor locations may be less dependent on an origin of particular brain signals, and therefore sensors may be more conveniently integrated with hardware (e.g., for looser fitting AR glasses).

As discussed herein, an image of significance (to a particular unique individual) in visual images 202 may be temporally correlated with a different image and/or visual stimulus in visual images 202 such that such a different image evokes a detectable brain signal that is temporally correlated with a P300 signal generated by human subject 200 responsive to such an image of significance. For example, such a different image or other visual stimulus in images 202 may comprise an image or visual stimulus capable of evoking a detectable brain signal as a so-called steady-state visual evoked potential (SSVEP) brain signal in human subject 200 (e.g., which are detectable by sensors 210 and/or 212). In an embodiment, SSVEP brain signals may comprise responses to visual stimulation at specific frequencies. For example, a human retina excited by a visual stimulus having a temporal frequency ranging from 3.5 Hz to 75 Hz may initiate electrical activity in a human brain at the same (or multiples of) frequency of such a visual stimulus.

In this particular implementation, in addition to applying a first sensory stimulus as a visual image of significance to a particular unique individual, series of visual images 202 may apply a second sensory stimulus comprising one or more visual images and/or visual stimuli that are temporally correlated with such a visual image of significance to a particular unique individual. For example, a second sensory stimulus may comprise presentation of a visual image in a series of visual images 202 that precedes or follows a visual image of significance to a particular unique individual by a predetermined and/or set time lag. Additionally, a visual image and/or visual stimuli providing a second sensory stimulus may comprise one or more frequency components having a predetermined and/or known frequency to evoke in human subject 200 a corresponding detectable SSVEP brain signal. Such an SSVEP brain signal may be temporally correlated with a P300 signal evoked in human subject 200 responsive to a visual image of significance to a particular unique individual in series of images 202. For example, detection of such an SSVEP brain signal may lead or lag detection of a P300 signal by a known or predetermined duration. In an embodiment, an inference that an identity of human subject 200 is an identity of a particular unique individual may be based, at least in part, on detection of a signal classified as a P300 brain signal (e.g., indicating an involuntary response by such a particular unique individual) may be confirmed based, at least in part, on detection of an SSVEP brain signal at a particular time relative to a time of detection of such a signal classified as a P300 brain signal.

According to an embodiment, a signal detected as an SSVEP brain signal may be temporally correlated with a signal initially classified as a P300 brain signal, at least in part, on features in such a signal detected as an SSVEP brain signal. One such feature in a signal detect as an SSVEP brain signal (to be temporally correlated with a signal initially classified as a P300 brain signal) may include a frequency characteristic such as a temporal frequency that is an integer multiple of a temporal frequency in a corresponding visual stimulus. Another such feature in a signal detected as an SSVEP signal (to be temporally correlated with a signal initially classified as a P300 brain signal) may include a variation in a signal magnitude, for example.

Figure 3:
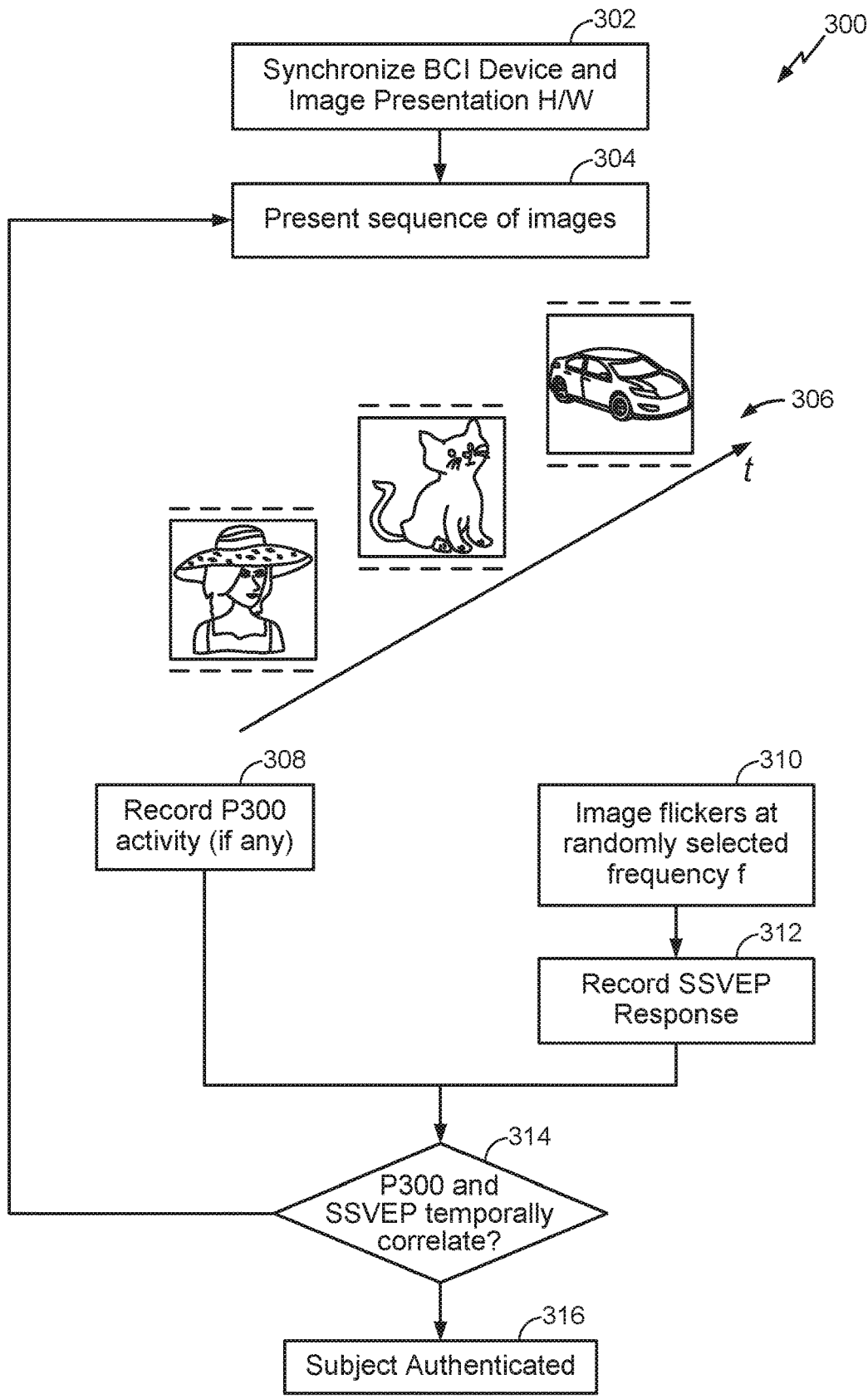
FIG. 3 is a flow diagram of an example process to electronically authenticate an identity of a subject according to an embodiment.

In an embodiment, an inference that an identity of human subject 200 is an identity of a particular unique individual based, at least in part, on detection of a signal classified as a P300 brain signal (e.g., indicating an involuntary response by the particular unique individual) may be confirmed based, at least in part, on detection of an SSVEP brain signal at a particular time relative to a time of detection of such a signal classified as a P300 brain signal (as illustrated in process 300 according to FIG. 3). For example, if such a signal classified as a P300 brain signal is detected at a time $t_e$, an SSVEP brain signal is detected at a time $t_2$ and detection of the P300 brain signal is expected to lead detection of the SSVEP brain signal by a duration $\Delta$, an identity of human subject 200 may be confirmed to be authenticated as being an identity of a particular unique individual if a condition set forth in expression (1) is satisfied. Alternatively, if such a signal classified as a P300 brain signal is detected at a time $t_e$, an SSVEP brain signal is detected at a time $t_2$ and detection of the P300 brain signal is expected to lag detection of the SSVEP brain signal by a duration $\Delta$, an identity of human subject 200 may be confirmed to be authenticated as an identity of a particular unique individual if a condition set forth in expression (2) is satisfied.

As pointed out above, values for $\Delta$ as applied in expressions (1) and (2) may vary based, at least in part, on a physiology of a particular unique individual. For example, a difference between presentation of a visual image of significance and detection of a responsive P300 brain signal may vary based on human physiology. For example, physiology of a particular human may uniquely affect a latency in processing a visual image commencing with exposure of a retina of such a particular human, followed by cognitive recognition of such an image captured at the retina and followed by generation of a P300 brain signal responsive to such cognitive recognition. Likewise, a difference between presentation of a visual stimulation at a particular temporal frequency and detection of a responsive SSVEP brain signal may vary based on human physiology. As such, a value for 4 may be determined and/or selected based, at least in part, expected response times by a particular unique individual to presentation of a visual image of significance and visual stimulation at a particular temporal frequency.

It may be observed that in particular implementations, particular characteristics of an SSVEP brain signal generated by a human (e.g., responsive to a visual stimulus at a particular temporal frequency) may be affected by a physiology of such a human. For example, a particular frequency characteristic in an SSVEP brain signal (e.g., a frequency shift at an integer multiple of a temporal frequency of a visual stimulus) may vary from individual to individual in a predictable manner. Additionally, a gain in magnitude of a voltage level of an SSVEP brain signal may vary from individual to individual. Thus, in an embodiment, an SSVEP brain signal generated by a particular unique individual may have features that are unique for that particular unique individual. Accordingly, in addition to evaluating a temporal correlation of a detected P300 brain signal and a detected SSVEP brain signal, a process may further compare features of such a detected SSVEP brain signal with features expected in an SSVEP brain signal (e.g., magnitude of frequency shift or voltage level) for a particular unique individual. In one particular implementation, a neural network processor may process observations of features of SSVEP brain signals by a particular unique individual over time. Based, at least in part, on the processed observations of the SSVEP brain signals, the neural network processor may be adapted to, individually or in combination with a temporal correlation of a detected P300 brain signal in a human subject, authenticate an identity of the human subject as being an identity of the particular unique individual.

In a particular implementation, one or more operations illustrated in FIG. 3 may be performed and/or executed at least in part by elements or features of a system shown in FIG. 2A (e.g., computing device 214, MUX 216, ADC 220, display devices, etc.). Block 302 may comprise synchronization of a brain computer interface (BCI) with signals controlling timing of presentation of a sequence of visual images such as visual images 202 through image presentation hardware such as display device 224. As pointed out above in the particular implementation of FIG. 2A, computing device 214 may comprise circuitry to maintain a clock state for controlling timing of presentation of visual images 202 in a particular sequence. MUX 216 may, in a particular implementation, comprise circuitry to maintain a clock state for use in determining time stamps to be applied to observations of brain signals detected based, at least in part, on voltage and/or current signals generated by sensors 210 and 212. Here, using message signalling, computing device 214 and MUX 216 may exchange messages to synchronize clock states maintained at computing device 214 and MUX 216 to a common time reference. This may enable time stamps applied to observations of brain signals detected based, at least in part, on voltage and/or current signals generated by sensors 210 and 212 to be temporally associated with images presented to human subject 200 according to such a common time reference.

According to an embodiment, block 304 may comprise presentation of visual images 306 to a human subject by applying signals to one or more display devices. As pointed out above, block 304 may present to a human subject at least some visual images 306 at known instances according to a time reference. For example, block 304 may present a visual image of significance (e.g., evoking a P300 brain signal in a human subject) in visual images 306 at a particular known time (e.g., according to the time reference). While visual images 306 are presented to a human subject via one or more display devices, detectable brain signals generated by such a human subject may be monitored based, at least in part, on voltage and/or current signals generated by sensors (e.g., sensors 210 and/or 212) positioned on particular locations of a scalp of a human subject.

In one particular implementation, while visual images 306 are being presented to a human subject, one or more sensors may be positioned to be in contact with one or more locations of such a human subject's scalp to detect and/or particular brain signals of interest (e.g., P300 brain signals and/or SSVEP brain signals described above). Block 308 may continually monitor voltage and/or current signals from one or more sensors to detect generation of a P300 brain signal by a human subject. As discussed above, detection of such a P300 brain signal may occur responsive to an involuntary response by a human subject to a particular visual image among visual images 306 that is of particular relevance or significance to a particular unique individual (e.g., a portrait of a family member, childhood scene or other image that potentially evokes an "attention grabbing" response in the particular unique individual).

As discussed above, in addition to including a visual image of significance (e.g., evoking generation of a P300 brain signal in a brain of a particular unique individual), visual images 306 may include another, different visual image and/or visual stimulus expected to precede or follow the visual image significance by a predetermined and/or known time lag. In an embodiment, a visual image of significance in visual images 306 may be presented to a human subject for a suitable duration to enable a reliable detection of a P300 brain signal in such a human subject. Following beginning of a presentation of a visual image of significance in visual images 306, block 310 may inject and/or induce a "flicker" in*presentation of the visual image of significance at a particular frequency. For example, a visual image of significance in visual images 306 may be presented for 0.5 seconds followed by a flickering of the visual image of significance at a particular frequency (e.g., a particular frequency "f") as indicated by block 310. Block 312 may comprise detecting an involuntary response from a human subject to flickering of a visual image of significance at block 310. For example, block 312 may detect an SSVEP brain signal having a frequency component that is at a particular frequency at which this visual image is flickered at block 310 or some multiple thereof.

Since flickering of a visual image of particular significance to a particular unique individual commences at block 310 a predetermined and/or known time lag following commencement of presentation of such a visual image of significance (e.g., 0.5 seconds), detection of a P300 brain signal at block 308 (occurring at about 300 msec following commencement of presentation of such a visual image of significance) and detection of a SSVEP brain signal at block 312 may occur roughly simultaneously or at a predetermined and/or known separation in time. As pointed out above, a predetermined and/or known separation of time between detections of a P300 brain signal at block 308 and an SSVEP brain signal at block 312 may vary depending on factors such as a particular physiology of a human subject receiving presentation of the visual stimulus. Accordingly, a genuine detection of a P300 signal at block 308 responsive to presentation of visual image of particular significance to a particular unique individual should be expected to be accompanied by detection of a corresponding SSVEP brain signal at block 312 at a predetermined and/or known delay and signal magnitude.

Diamond 314 may perform an association of activity recorded at blocks 308 and 310 to confirm that a signal classified as a P300 brain signal is indeed a P300 brain signal evoked as an involuntary response to a sensory stimulus. Referring to expression (1) and (2) above, a time of detection at block 308 of a signal classified as a P300 brain signal may have a value $t_e$, a time of detection at block 310 of an SSVEP signal at block 312 may have a value of $t_2$ and an expected difference between a time of detection ($t_1$) of an actual P300 brain signal at block 308 and detection of an SSVEP signal at block 310 may have a value A. If detection of a brain signal classified as a P300 brain signal at block 308 is expected to lead detection of an SSVEP signal at block 310 by A, diamond 314 may then determine whether the signal classified as a P300 brain signal is indeed a P300 brain signal (evoked in the brain of a particular unique individual) if the condition of expression (1) is satisfied. Likewise, If detection of the P300 brain signal at block 308 is expected to lag detection of an SSVEP signal at block 310 by Δ, diamond 314 may then determine whether a signal classified as a P300 brain signal is indeed a P300 brain signal (evoked in a brain of a particular unique individual) if a condition of expression (2) is satisfied. In either case, block 316 may authenticate an identity of a human subject as an identity of a particular unique individual.

As pointed out above, diamond 314 may temporally correlate a signal recorded as an SSVEP brain signal at block 312 with a signal recorded as a P300 brain signal at block 308 based, at least in part, on features in such a signal recorded as an SSVEP brain signal at block 312. For example, diamond 314 may comprise temporally correlating an occurrence of a frequency characteristic in such a signal recorded as an SSVEP brain signal at block 312 (such as a temporal frequency that is an integer multiple of a temporal frequency in a corresponding visual stimulus) and/or occurrence of signal magnitude variation in such a signal recorded as an SSVEP brain signal at block 312.

As pointed out above, in addition to a temporal correlation determined at diamond 314, in a particular implementation authentication of a subject at block 316 may be further based on features of an SSVEP signal recorded at block 312. As pointed out above, features of an SSVEP signal recorded at block 312 (e.g., magnitude of frequency shift in SSVEP signal based on particular flicker frequency "f" and magnitude in signal voltage variation) may vary based on particular physiological characteristics of a human subject. Accordingly, to obtain further confidence in an authentication, block 316 may further determine whether features in an SSVEP brain signal recorded at block 312 sufficiently match expected features in an SSVEP brain signal evoked in a particular unique individual responsive to flickering in an image at block 310.

Figure 4:
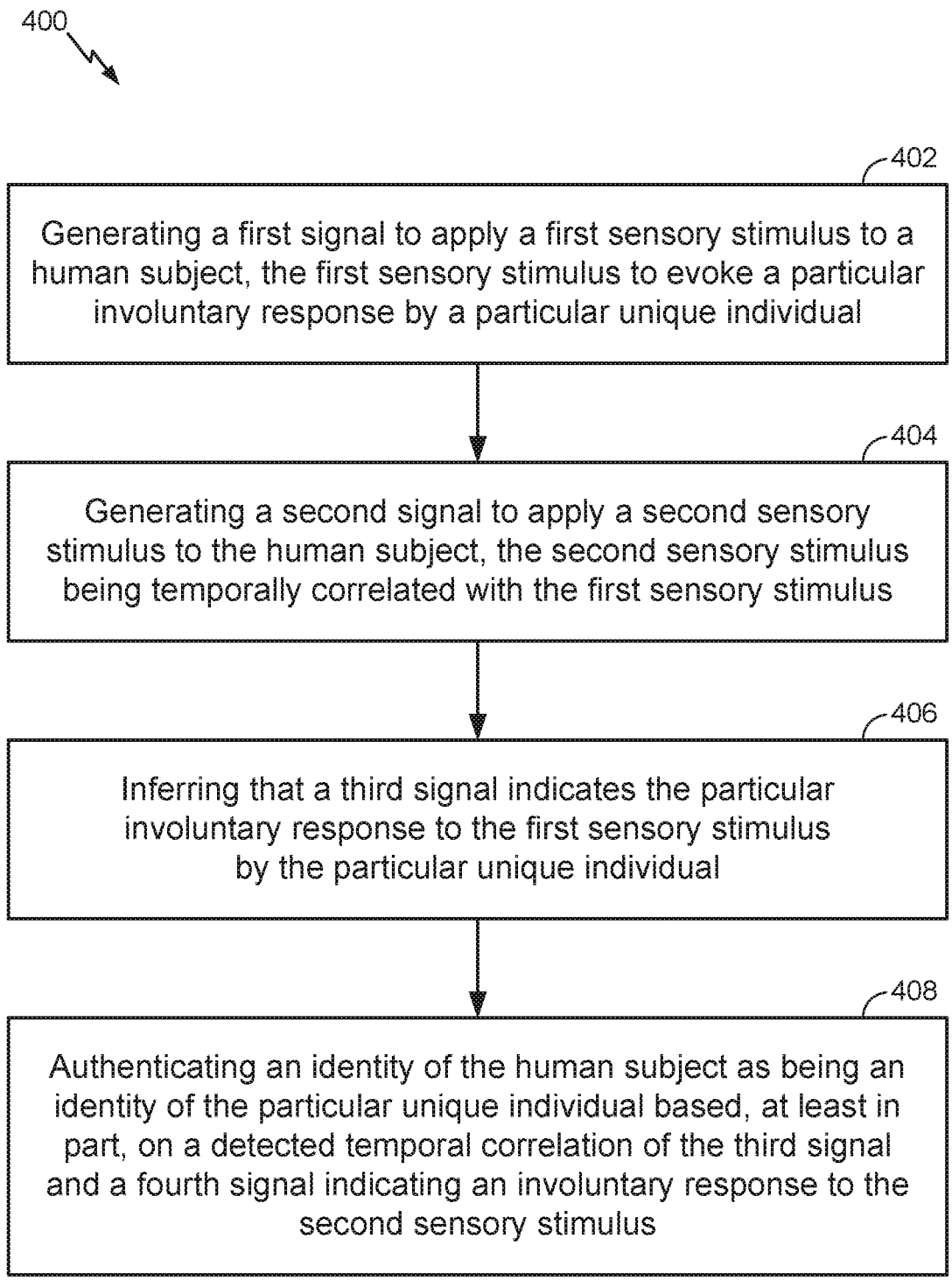
FIG. 4 is a flow diagram of an aspect of an example process to electronically authenticate an identity of a subject according to an embodiment.

FIG. 4 is a flow diagram of an aspect of a process 400 that may be implemented at least in part to facilitate and/or support one or more operations and/or techniques to electronically authenticate an identity of a human subject according to an embodiment. It should be noted that information acquired or produced, such as, for example, input signals, output signals, operations, results, etc. associated with example process 400 may be represented via one or more digital signals. It should also be appreciated that even though one or more operations are illustrated or described concurrently or with respect to a certain sequence, other sequences or concurrent operations may be employed. In addition, although the description below references particular aspects and/or features illustrated in certain other figures, one or more operations may be performed with other aspects and/or features. Thus, example process may, for example, begin at block 402 with generating a first signal to apply a first sensory stimulus to a human subject. For example, block 402 may comprise computing device 214 of FIG. 2A generating a signal to display device 224 for presentation of a visual image of significance to human subject 200, such as to evoke generation of a phenomenon responsive to a cognitive functioning in a brain of human subject 200 (e.g., P300 brain signal, phenomena detectable by a MEG scan, eye movement, pupillary response, heartbeat, etc.). As pointed out above, such a visual image of significance may comprise an image of significance to a particular unique individual. For example, such an image of significance to a particular unique individual may comprise a portrait of a family member, childhood scene or other image, just to provide a few examples, that potentially evokes an "attention grabbing" response in such a particular unique individual. It should be understood, however, that in alternative embodiments a first sensory stimulus to a human subject applied by block 402 may comprise providing content and/or control signals to specific devices (e.g., speakers, haptic devices, etc.) to apply audible sounds or a haptic stimulus (e.g., application of light pressure or vibrations to various locations of a scalp of a human subject), just to provide a few examples of additional sensory stimuli that may evoke a corresponding detectable or measurable involuntary response in a human subject.

As discussed herein in connection with a particular implementation, a first signal may be generated at block 402 from an electronic document maintained in a library stored on one or more device-readable storage mediums. In an example, a computing device (such as computing device 214 as shown in FIG. 2A) may fetch an electronic document from a device-readable medium, and execute device readable instructions to generate a first signal. In an embodiment, an electronic document may be stored in a library of electronic documents maintained on a device-readable medium and may be fetched based, at least in part, on a unique identifier associated with a particular unique individual. For example, a fetched electronic document may be accessed from a library based, at least in part, on an associated identifier such as a first/last name, social security number and/or other personal attributes unique to a particular unique individual, just to provide a few examples. According to an embodiment, a fetched electronic document may comprise media content (e.g., still images, audio, video, etc.) encoded in a particular format (e.g., JPEG, MPEG, MP3, etc.). By execution of device readable instructions, a computing device executing block 402 may decode portions of a fetched electronic document to provide a first signal as control and/or content signals to one or more output devices for applying sensory stimuli to a human subject. For example, block 402 may construct a signal to drive a display device (e.g., display device 224) for presentation of a series of video frames based, at least in part, on media content in an electronic document that has been decoded. In an alternative implementation, a first signal generated at block 402 (e.g., to drive a display device) may be based, at least in part, on media content obtained via a generative adversarial network (GAN) which has been trained to generate images and/or audio content of a specific "type" that is likely to evoke a physiological phenomenon in a particular unique individual. As pointed out above, such a series of video frames may present one or more images of particular significance to a particular unique individual (e.g., potentially evoking a P300 brain signal in such a particular unique individual). In an example implementation, video frames presented responsive to the first signal may be temporally interleaved with other video frames presenting images other than visual images of particular significance to a particular unique individual (e.g., to enable detection of a P300 brain signal according to the aforementioned odd-ball paradigm).

Block 404 may comprise generating a second signal to apply a second sensory stimulus to a human subject that is temporally correlated with a first sensory stimulus applied based, at least in part, on such a first signal generated by block 402. For example, block 404 may be executed at least in part by computing device 214 generating a signal to a display device (e.g., display device 224) for presentation of a second visual image at a set duration preceding or following generation of a first visual image. As pointed out above, an involuntary response to a first sensory stimulus applied at block 402 may comprise a phenomenon generated responsive at least in part to a cognitive functioning in a brain of a human subject (e.g., a P300 brain signal, occurring in a brain of a human subject, phenomena detectable by a MEG scan, eye movement, pupillary response, heartbeat, etc.). A second visual image may comprise a visual image having a temporal frequency component evoking a detectable SSVEP brain signal in such a human subject. For example, such a second visual image may comprise a flickering of a first visual image at a randomly selected frequency and beginning at a known duration following a start of a presentation of such a first visual image such as at block 310. In an implementation, a computing device (e.g., computing device 214) may execute instructions fetched from a device-readable medium to effect a flickering of an image at a particular or predetermined temporal frequency.

In a particular implementation in which block 402 constructs a first signal to drive a display device and/or speaker for presentation of one or more visual images and/or sounds from a series of and/or video frames, block 404 may comprise modifying a portion of video frames in such a series of video frames. For example, a computing device may construct a media and/or control signal comprising a series of video frames including a first portion of video frames to present one or more visual images of particular significance to a particular unique individual. Block 404 may comprise a modification to a second portion of video frames at a predetermined or known temporal separation from such a first portion of video frames. In an implementation, such a second portion of video frames may be modified by imparting a flickering (or other image distortion) in generated visual images (e.g., at a known frequency) to evoke a response (e.g., brain signal such as an SSVEP brain signal or other physiological phenomenon) in a human subject.

Block 406 may comprise determining that a collected third signal indicates that a particular involuntary response by a human subject to a first sensor stimulus applied at block 402. As pointed out in a particular implementation, a sensor positioned at a particular location of a human subject's scalp may generate voltage and/or current signals indicative of or responsive to involuntary responses (e.g., brain signals) to sensory stimuli. As pointed out above, such one or more sensors may comprise any one of several electrodes suitable for non-invasive placement on a human scalp to support electroencephalography (EEG) brain signal processing. It should be understood, however, that one or more third signals may be generated at block 406 by different types of sensors including, for example, sensors capable of detecting and/or measuring other types of involuntary responses as discussed herein. In a particular example, block 406 may infer that such a third signal is indicative of and/or generated responsive to an occurrence of a P300 brain signal evoked responsive to such a first sensory stimulus applied at block 402. For example, block 406 may comprise recording of P300 brain signal activity at block 308.

According to an embodiment, in some instances, an inference at block 406 that a third signal indicates an involuntary response to a first sensory stimulus by a particular unique individual may be false. For example, block 406 may comprise detection of a signal having one or more attributes of a P300 brain signal at block 308, which may or may not comprise a correct positive detection of a P300 brain signal. Further processing may provide additional confidence that a collected third signal (e.g., appearance of a P300 brain signal based, at least in part, on activity detected at block 308) indeed is a particular involuntary response by a particular unique individual of interest. Block 408 may comprise authenticating an identity of a human subject as being an identity of a particular unique individual based, at least in part, on a detected temporal correlation of a third signal and a fourth signal indicating an involuntary response (e.g., an involuntary response which matches a given individual's expected or predetermined response stored in a repository expected responses) to a second sensory stimulus applied at block 408. In an implementation, block 408 may determine a detected temporal correlation of a third signal and fourth signal as illustrated at diamond 314. For example, a third signal may comprise a P300 brain signal detected by block 308 at a time $t_e$, a fourth signal may comprise an SSVEP brain signal detected by block 312 at time $t_2$ and an expected lag between detection of a P300 brain signal and temporally correlated SSVEP brain signal may be $\Delta$. If detection of a third signal would be expected to lead detection of a fourth signal, an identity of a human subject may be confirmed to be authenticated as being an identity of a particular unique individual if the condition of expression (1) is met. Likewise, if detection of a third signal would be expected to lag detection of the fourth signal, the identity of the human subject may be confirmed to be authenticated as being an identity of a particular unique individual if the condition of expression (2) is met.

In a particular implementation, block 408 may further base authentication of an identity of a human subject, at least in part, on features in a fourth signal. As pointed out above, such a fourth signal may comprise an SSVEP brain signal with signal characteristics (e.g., magnitude of frequency shift and voltage) that may vary based, at least in part, on a particular physiology of a human subject. Here, block 408 may further base authentication of an identity of a human subject, at least in part, on whether features in such a fourth signal sufficiently match features in a fourth signal that would be expected if evoked in a unique particular individual responsive to a second sensory stimulus. For example, if such a fourth signal comprises an SSVEP brain signal evoked in a human subject responsive to a second sensory stimulus, block 408 may further base authentication of an identity of a human subject as being an identity of a particular unique individual, at least in part, on whether a magnitude in frequency response and/or voltage in the SSVEP brain signal sufficiently match an expected magnitude in frequency response and/or voltage in an SSVEP brain signal to be evoked by such a particular unique individual responsive to such a second sensory stimulus.

As pointed out above, block 402 may retrieve an electronic document fetched from a library of electronic documents stored on a device-readable medium. In addition to containing media content for use in generating a first signal, such an electronic document may comprise one or more additional parameters corresponding to a particular unique individual for application by block 408 in authentication of an identity of a human subject. For example, such an electronic document may comprise a value for Δ to be applied in expression (1) or (2) in determining whether the third signal (e.g., signal detected as a P300 brain signal) temporally correlates with a fourth signal (e.g., SSVEP brain signal). A value for Δ may be determined and/or selected based, at least in part, on expected response times by a particular unique individual to first and second sensory stimuli (e.g., based, at least in part, on expected response times by a particular unique individual to presentation of a visual image of significance to evoke a P300 brain signal and visual stimulation at a particular temporal frequency to evoke an SSVEP brain signal). In addition to containing media content for use in generating a first signal and/or a value for Δ, an electronic document may comprise additional parameters corresponding to expected features in a fourth signal if evoked in a particular unique individual responsive to a second sensory stimulus. As discussed above, these parameters corresponding to expected features in a fourth signal (e.g., magnitude of frequency shift and/or voltage in an SSVEP signal) may then be compared with actual features in a fourth at block 408 for added confidence in an authentication of an identity of a human subject.

According to an embodiment, values for Δ stored in an electronic document may be initially determined in a training process in which repeated stimuli may be applied to a particular unique individual, such as while brain signals are monitored and measured, for example. Likewise, one or more additional parameters stored in an electronic document corresponding to expected features in a fourth signal (e.g., magnitude of frequency shift and/or voltage in an SSVEP signal) may be determined in a training process in which a second stimulus is repeatedly applied to such a particular unique individual while brain signals are monitored and measured. For example, such a training process may determine that a particular unique individual doesn't have the same response if the particular unique individual is somewhat agitated, etc. In an implementation, pulse rate, perspiration, body temperature, pupillary response and/or eye movement, for example may be used to determine whether a particular unique individual is agitated, and therefore likely to elicit a different type of response.

As may be observed, one or more particular implementations of processes 300 and 400 may enable authentication of an identity of a human subject based, at least in part, on observations of involuntary processes of such a human subject (e.g., based on signals from sensors monitoring such involuntary processes). This may be accomplished at least in part by processing and/or combining of sensors signals indicative of observations of involuntary processes of such a human subject. This may reduce or eliminate reliance on voluntary actions by a human subject (e.g., entering a password to a keypad, speaking, interacting with a biometric sensing device, etc.), such as in a process to authenticate an identity of such a human subject. Additionally, processes 400 and 800 refer to human subject as an example, subject for authentication. In other implementations, such a subject for authentication need not be a human subject, but may instead comprise a non-human (e.g., non-human mammal capable of generating detectable physiological phenomenon responsive at least in part to cognitive functioning).

Figure 5:
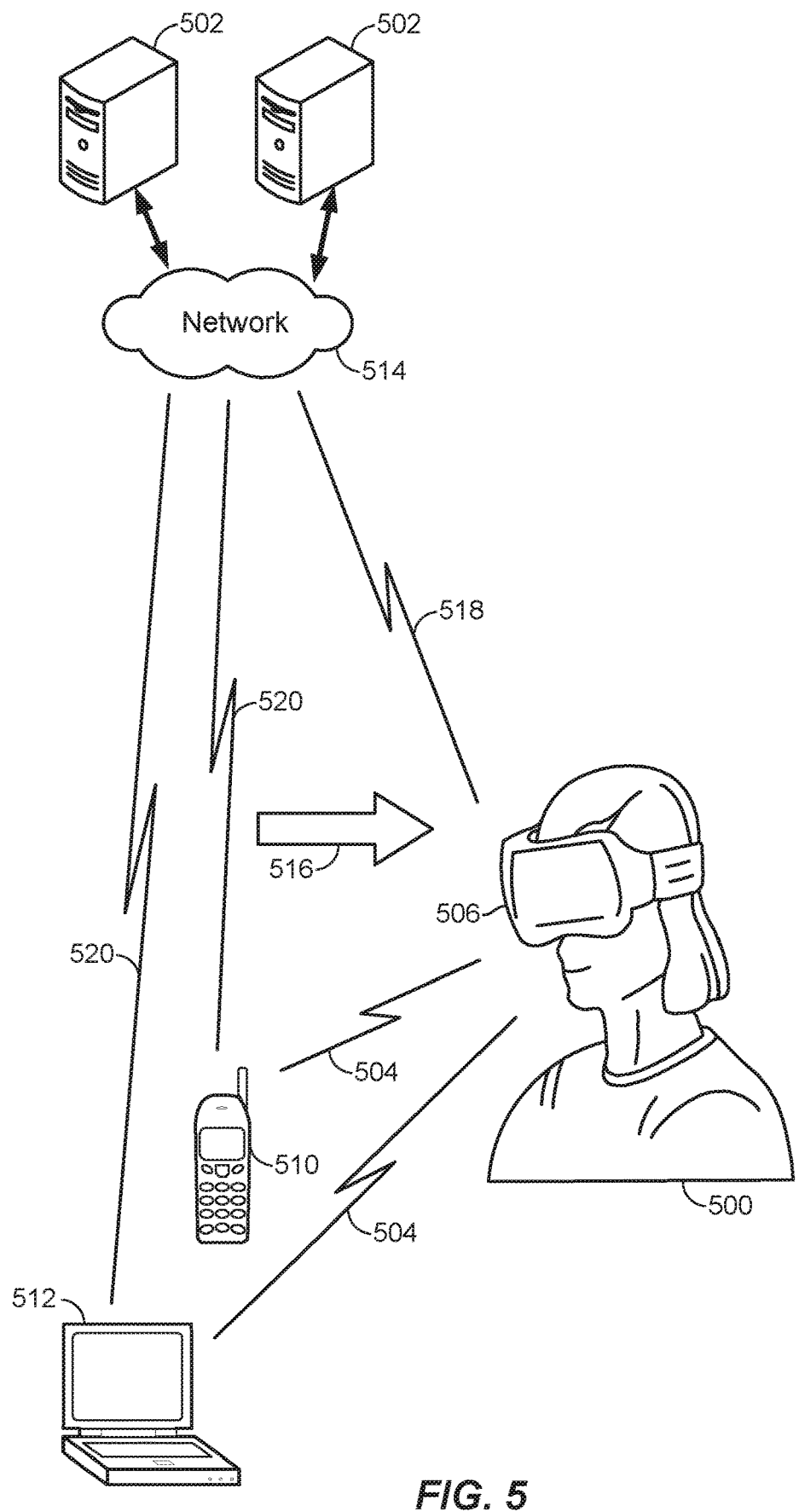
FIG. 5 is a schematic diagram of an example system to electronically authenticate an identity of a subject according to an alternative embodiment.

Embodiments discussed above are directed to, among other things, a system, process and/or device for authentication of an identity of a human subject based, at least in part, on an involuntary response of the human subject to predetermined sensory stimuli. In another embodiment as shown in FIG. 5, an identity of a human subject 500 may be authenticated based, at least in part, on an expected involuntary response by human subject 500 to observed aspects of an immediate environment experienced by human subject 500. Such sensory stimuli in and/or imparted by an immediate environment may include, for example, sights, sounds, odors, ambient light, ambient temperature, humidity, atmospheric pressure, etc., that may (individually or in combination) evoke one or more particular involuntary responses in a particular unique individual that experiences such an immediate environment. Additionally, an immediate environment experienced by human subject 500 may be further contextualized by time of day, day of week, location (e.g., geographic location and/or location with in a building, structure or vehicle, etc.), or other aspects which may further contextualize an immediate environment experienced by human subject 500.

According to an embodiment, sensory stimuli of an immediate environment experienced by human subject 500 may evoke a detectable and/or measurable involuntary response by a particular unique individual that is unique to that particular unique individual. In other words, sensory stimuli of an immediate environment may evoke a particular involuntary response in a particular unique individual that may not likely be evoked in another, different human subject.

As discussed above, images, sounds and/or other sensory stimuli of particular significance to a particular unique individual (e.g., images and/or voice of familiar people, sounds, familiar locations, etc.) may evoke in such a particular unique individual a particular involuntary response (e.g., P300 brain signal and/or other physiological phenomenon generated at least in part responsive to cognitive functions). According to an embodiment, an immediate environment experienced by human subject 500 may provide images, sounds and/or other sensory stimuli of particular significance to a particular unique individual. One particular embodiment may comprise a determination of a likely response by a particular unique individual to features in an environment that may evoke a particular involuntary response in such a particular unique individual. If such a likely response by human subject 500 to such an environment is observed, an identity of human subject 500 may be authenticated as an identity of such a particular unique individual.

In the particular implementation of FIG. 5, human subject 500 may wear goggles and/or glasses 506 that enable presentation of an augmented reality experience to human subject 500. In some implementations, googles and/or glasses 506 may comprise, or be incorporated as part of, an AR and/or VR headset. Alternatively, one or more features of googles and/or glasses 506 may be incorporated in headphones and/or a mobile phone. In an implementation, goggles and/or glasses 506 may comprise one or more display devices (e.g., placed over eyes of human subject 500) (not shown) to present an image of a current line of light view of human subject 500. As part of providing an augmented reality experience, one or more images may be laid over and/or combined with such an image of a current line of sight view presented to human subject 500. For example, goggles and/or glasses 506 may comprise an affixed camera (not shown) to capture a moving image of such a current line of light view of human subject 500 (e.g., controlled or determined at least in part from detected and/or measured eye movements). Signals to represent such a captured moving image may then be combined with signals representing other images (e.g., text, animated objects in a scene, arrows for direction, menus when approaching shops, creatures from games and/or audio and/or images in video conferencing, elements of a computer generated AR and/or VR experience, etc.) for generation of images to be presented to human subject 500 through display devices of goggles and/or glasses 506 as part of providing an augmented reality experience. Goggles and/or glasses 506 may also comprise one or more speakers and/or associated amplification circuitry (not shown) to provide audible sounds to human subject 500 as part of an augmented reality experience.

According to an embodiment, goggles and/or glasses 506 may further comprise first sensors (not shown) to detect and/or measure involuntary responses of human subject 500 to sensory stimuli 516 applied to and/or experienced by human subject 500. For example, goggles and/or glasses 506 may be integrated as part of a headset that includes sensors (not shown) to be positioned on locations of a scalp of human subject 500 to detect and/or measure brain signals of interest. In a particular implementation, goggles and/or glasses 506 may be integrated as part of a headset that includes first sensors to be positioned on particular locations of a scalp as shown in FIG. 2B and as described above. One or more features of goggles and/or glasses 506 may be implemented in a head mounted display and/or headphones, for example. First sensors of goggles and/or glasses 506 may also comprise additional sensors capable of detecting other involuntary responses such as, for example, a heart rate and/or heartbeat monitor, sensors enabling MEG scans, perspiration monitor, body thermometer, sensors capable of detecting a pupillary response, sensors capable of detection eye movement and/or blinking (e.g., eye tracker), just to provide a few examples. Alternatively, one or more of these first sensors need not be integrated with goggles and/or glasses 506 but may instead be in communication with processing circuitry (not shown) of goggles and/or glasses 506 over a communication link (e.g., over a Bluetooth® or Near Field Communication link).

Goggles and/or glasses 506 may further comprise second sensors which are responsive to and/or capable of measuring and/or detecting aspects of an environment experienced by human subject 500 such as sensory stimuli 516. For example, in addition to a camera as indicated above, goggles and/or glasses 506 may also comprise environmental sensors (not shown) such as, for example, one or more ambient temperature thermometers, light sensors, barometers, humidity detectors, microphones, just to provide a few examples. Goggles and/or glasses 506 may also further comprise inertial sensors such as accelerometers or gyroscopes for use in detecting motion and/or three-dimensional orientation of goggles and/or glasses 506. In an embodiment, signals generated by from such inertial sensors may enable detection of tilt and/or orientation of a head of human subject 500 relative to objects in an immediate environment. In addition, goggles and/or glasses 506 may comprise one or more radio frequency receivers (not shown) capable of receiving and processing positioning signals (e.g., signals transmitted from a global navigation satellite system) for use in determining and/or characterizing a location of goggles and/or glasses 506.

According to an embodiment, an environment experienced by human subject 500 may be characterized, at least in part, by objects recognized in images captured by a camera of goggles and/or glasses 506, signals obtained from other sensors integrated with goggles and/or glasses 506 (e.g., environmental sensors and/or motion sensors as identified above), a location (e.g., geographical location, location within a building, structure or vehicle, etc. as determined based, at least in part, on positioning signals received at goggles or glasses 506), time of day and/or day of week, just to provide a few examples.

Additionally, an involuntary response by human subject 500 to sensory stimuli 516 of an environment experienced by human subject 500 may be characterized based, at least in part, on signals generated by one or more of the aforementioned first sensors (e.g., brain signals, measurements of body temperature, heart rate, pupillary response, blood pressure or perspiration and/or observations of eye movements, etc.). As discussed below in a particular implementation, an identity of human subject 500 may be authenticated as being an identity of a particular unique individual based, at least in part, on a characterization of an environment experienced by human subject 500 and an involuntary response of human subject 500 to such an environment experienced by human subject 500.

According to an embodiment, all or a portion of a process to authenticate an identity of human subject 500 as being an identity of a particular unique individual may be performed, in whole or in part, by remote computing device(s) 502. According to an embodiment, remote computing device(s) 502 may comprise remote computing devices (e.g., such as computing devices 902, 904 and/or 906 shown in FIG. 9 and described below) capable of executing device readable instructions stored in memory to perform all or portions of an authentication process. In an implementation, remote computing device(s) 502 may be arranged and/or configured to provide a cloud computing service. Wireless communication link 504 may be used to transmit message signals between remote computing device(s) 502 and goggles and/or classes 506. In an alternative implementation, wireless communication link 504 may be replaced with a cable connection. Wireless communication links 508 between goggles and/or glasses 506 may enable transmission of message signals between goggles and/or glasses 506 and devices local to goggles and/or glasses 506 such as, for example, such as mobile phone 510, laptop computer 512, wearable devices (not shown) (e.g., watch), just to provide a few examples. Also, wireless communication links 520 may enable transmission of message signals between remote computing device(s) 502 and devices accessible by human subject 500 such as mobile phone 510, laptop computer 512 and/or wearable devices (not shown). In an alternative implementation, other wireless communication links (not shown) may enable transmission of message signals between goggles and/or glasses 506 and remote sensors (e.g., sensors to monitor physiological responses of human subject 500 and/or sensors to observe aspects an immediate environment of human subject 500 (not shown) to characterize sensory stimuli.

According to an embodiment, an authentication result (e.g., authentication of an identity of human subject 500 as being an identity of a particular unique individual) may be applied to determine whether a human subject is authorized to access certain devices, obtain certain services and/or obtain a certain level of a service, just to provide a few examples. For example, an authentication result of a process to authenticate an identity of human subject 500 as being an identity of a particular unique individual may authorize human subject 500 to access local devices, access a bank account and/or receive a particular level of service, for example. In an implementation, a process to authenticate an identity of human subject 500 as being an identity of a particular unique individual may generate a key or token signal (e.g., transmitted from remote computing device(s) 502 or goggles and/or glasses 506) to be provided to a device to be accessed by human subject 500 (e.g., mobile phone 510, laptop computer 512 and/or wearable devices). If an authentication result is determined at remote computing device(s) 502, remote computing device(s) 502 may transmit a key or token signal in a message to a device to which access is to be authorized (e.g., transmission of a key or token signal in a wireless communication link 520 and/or 504) to glasses and/or goggles 506, mobile phone 510, laptop computer 512 and/or wearable devices). In another implementation, an authentication result may determine authorization of human subject 500 to receive a certain level of an augmented reality experience through goggles and/or classes 506. For example, such an authorization to receive a certain level of an augmented reality experience through goggles and/or glasses 506 may determine a presence and/or character of images to be laid over or combined with an image of a current line of sight view presented to human subject 500 as part of such an augmented reality experience.

Figure 6:
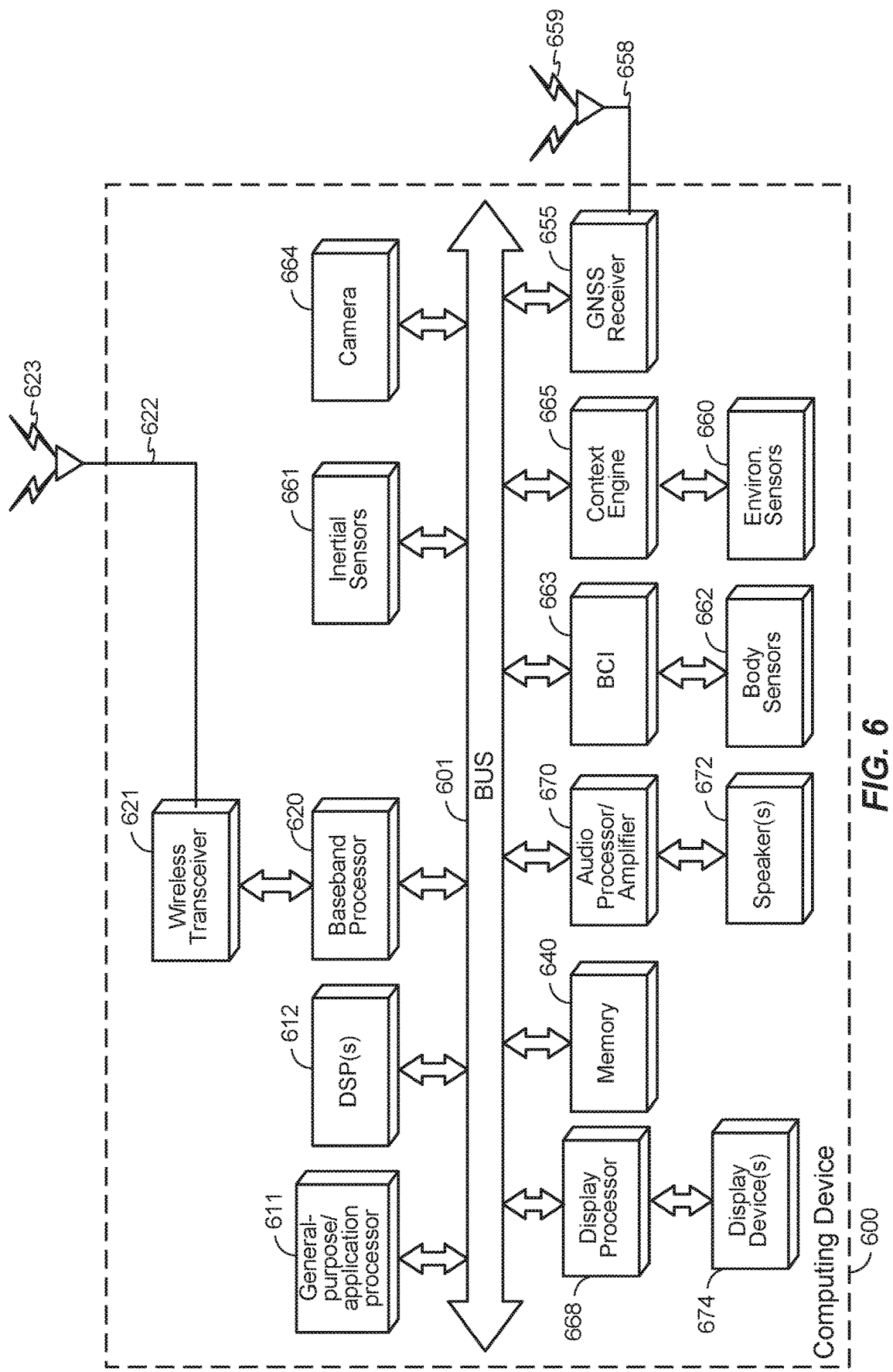
FIG. 6 is a schematic diagram of an example computing device for application to a process for electronic authentication of a subject according to an embodiment.

FIG. 6 is a schematic diagram of a computing device 600 for application to a process for authentication of an identity of a human subject according to an embodiment. In a particular implementation, all or a portion of features shown in FIG. 6 and described herein may be incorporated in goggles and/or glasses 506. Here, devices may be coupled to communicate on a signalling bus 601 according to any one of several bus protocols. General-purpose/application processor 611 may execute computer-readable instructions stored in memory 640 to, for example, perform all or a portion of a process to authentication an identity of a human subject and/or present an augmented reality experience to a human subject.

Baseband processor 620, radio frequency transceiver 621 and antenna 623 may enable bi-directional communication in one or more wireless communication links (e.g., wireless communication links 504, 508 and/or 520) with other devices (e.g., remote computing device(s) 502, mobile phone 510, laptop computer 512, wearable devices, etc.). Such a wireless communication link may be implemented using any one of several wireless communication techniques suitable for communication in a wireless wide area network (WWAN), a wireless local area network (WLAN), a wireless personal area network (WPAN), and so on. Such a WWAN may comprise a Code Division Multiple Access (CDMA) network, a Time Division Multiple Access (TDMA) network, a Frequency Division Multiple Access (FDMA) network, an Orthogonal Frequency Division Multiple Access (OFDMA) network, a Single-Carrier Frequency Division Multiple Access (SC-FDMA) network, or any combination of the above networks, and so on. A CDMA network may implement one or more radio access technologies (RATs) such as cdma2000, Wideband CDMA (WCDMA), to name just a few radio technologies. Here, cdma2000 may include technologies implemented according to IS-95, IS-2000, and IS-856 standards. A TDMA network may implement Global System for Mobile Communications (GSM), Digital Advanced Mobile Phone System (D-AMPS), or some other RAT. GSM and WCDMA are described in documents from a consortium named "3rd Generation Partnership Project" (3GPP). Cdma2000 is described in documents from a consortium named "3rd Generation Partnership Project 2" (3GPP2). 3GPP and 3GPP2 documents are publicly available. 4G Long Term Evolution (LTE) and 5G or New Radio (NR) communications networks may also be implemented in accordance with claimed subject matter, in an aspect. A WLAN may comprise an IEEE 802.11x network, and a WPAN may comprise a Bluetooth® network, an IEEE 802.15x, for example. Wireless communication implementations described herein may also be used in connection with any combination of WWAN, WLAN or WPAN.

Global navigation satellite system (GNSS) receiver 655 and antenna 658 may enable processing of signals transmitted from one or more GNSS' (e.g., while in an outdoor environment) such as, for example, US Global Positioning System (GPS), the European Galileo system or the Russian Glonass system to, for example, obtain a position fix including an estimated geographical location of GNSS receiver 655. In one alternative, general-purpose/application processor 611 may compute an estimated location based, at least in part, on terrestrial signals received at radio frequency transceiver 621 using any one of several positioning techniques including, but not limited to, heatmap signature matching, trilateration to three or more beacon devices. In another alternative, general-purpose/application processor 611 may compute an estimated location of computing device 600 based, at least in part, on processed images captured at camera 664 and/or processed signals received at inertial sensors 661 using dead reckoning from a known location and/or simultaneous localization and mapping (SLAM), for example. It should be understood, however, that these are merely examples of techniques that may be used to determine and/or estimate a location of a computing device (such as a computing device 600 integrated with goggles and/or glasses 506), and claimed subject matter is not limited in this respect.

According to an embodiment, general-purpose/application processor 611 may execute instructions stored on memory 640 to coordinate operation of camera 664, display processor 668, display device(s) 674, audio processor/amplifier 670 and speaker 672 to provide an augmented reality experience to a user (e.g., human subject 500) as discussed above. Computing device 600 may also comprise one or more other co-processing devices (not shown) to complete computing tasks under the control of and/or in conjunction with general-purpose application processor 611 such as, for example, a neural network processing unit and/or graphics processing unit. In an implementation, camera 664 may capture a moving image in a line of sight view of a human subject, and such a captured image may be presented to such a human subject in real-time through display device(s) 674 (e.g., positioned over such a human subject's eyes). As pointed out above, such an augmented reality experience may comprise presentation of an augmented image to a human user where the presented image comprises an alteration of a captured image and/or a captured image combined with additional images signals (e.g., visual text, objects overlaid in a scene, etc.). Contemporaneously with presentation of an augmented image in display device(s) 674, audio processor/amplifier 670 in combination with speaker(s) 672 may provide an audio signal as part of an augmented reality experience.

According to an embodiment, context engine 665 may process signals received from multiple devices including, for example, environmental sensors 660, inertial sensors 661, as well as real-time images captured at camera 664 to, for example, characterize an environment experienced by a human subject as discussed above. In one implementation, context engine 665 may comprise one or more processing devices to combine and/or fuse signals received from environmental sensors 660, signals received from inertial sensors 661 and images captured at camera 664 to, for example, determine one or more parameters characterizing an environment experienced by a human subject. For example, context engine 665 may determine parameters or features characterizing sensory stimuli in an environment experienced by a human subject, that may evoke a detectable and/or measurable involuntary response from a particular unique individual. In an implementation, context engine 665 may incorporate a location of computing device 600 (e.g., determined, estimated and/or characterized based, at least in part, on signals received at GNSS receiver 655 and processed at general-purpose/application processor 611) in characterizing an environment experienced by a human subject. According to particular embodiments, context engine 665 may be implemented, at least in part, as one or more specialized processing units such as, for example, neural network processing units and/or visual processing units. In a particular implementation, such specialized processing units may perform computing tasks in connection with context engine 665 under the control of and/or in conjunction with general-purpose application processor 611, for example.

According to an embodiment, body sensors 662 may comprise sensors to be positioned on particular locations of a scalp as shown in FIG. 2B to detect and/or measure brain signals, and/or sensors capable of detecting other involuntary responses such as, for example, a heart rate monitor, perspiration monitor, body thermometer, sensors capable of detection eye movement, pupillary response and/or blinking, as pointed out above. Brain computer interface (BCI) 663 may comprise devices such as a multiplexer, buffer/amplifier and analog-to-digital converter (e.g., such as MUX 216, buffer/amplifier 218 and ADC 220 as discussed above with reference to FIG. 2A). BCI 663 may be capable of combining signals generated by multiple source devices including, for example, body sensors 663. In one particular example, BCI 663 may comprise a machine-learning processor to assist in fusing, filtering or otherwise processing current and/or voltage signals generated by body sensors 662, and classification of detected signal characteristics for use in additional processing. In one particular implementation, BCI 663 may be adapted to implement one or more techniques for detection and classification of signals generated by one or more of the aforementioned body sensors 663 (e.g., P300 brain signals, MEG scans, eye tracking detections, pupillary response, heartbeats, heart rate, blood pressure, body temperature and/or perspiration, etc.) based, at least in part, on current and/or voltage signals generated by body sensors 663 as discussed above.

Figure 7:
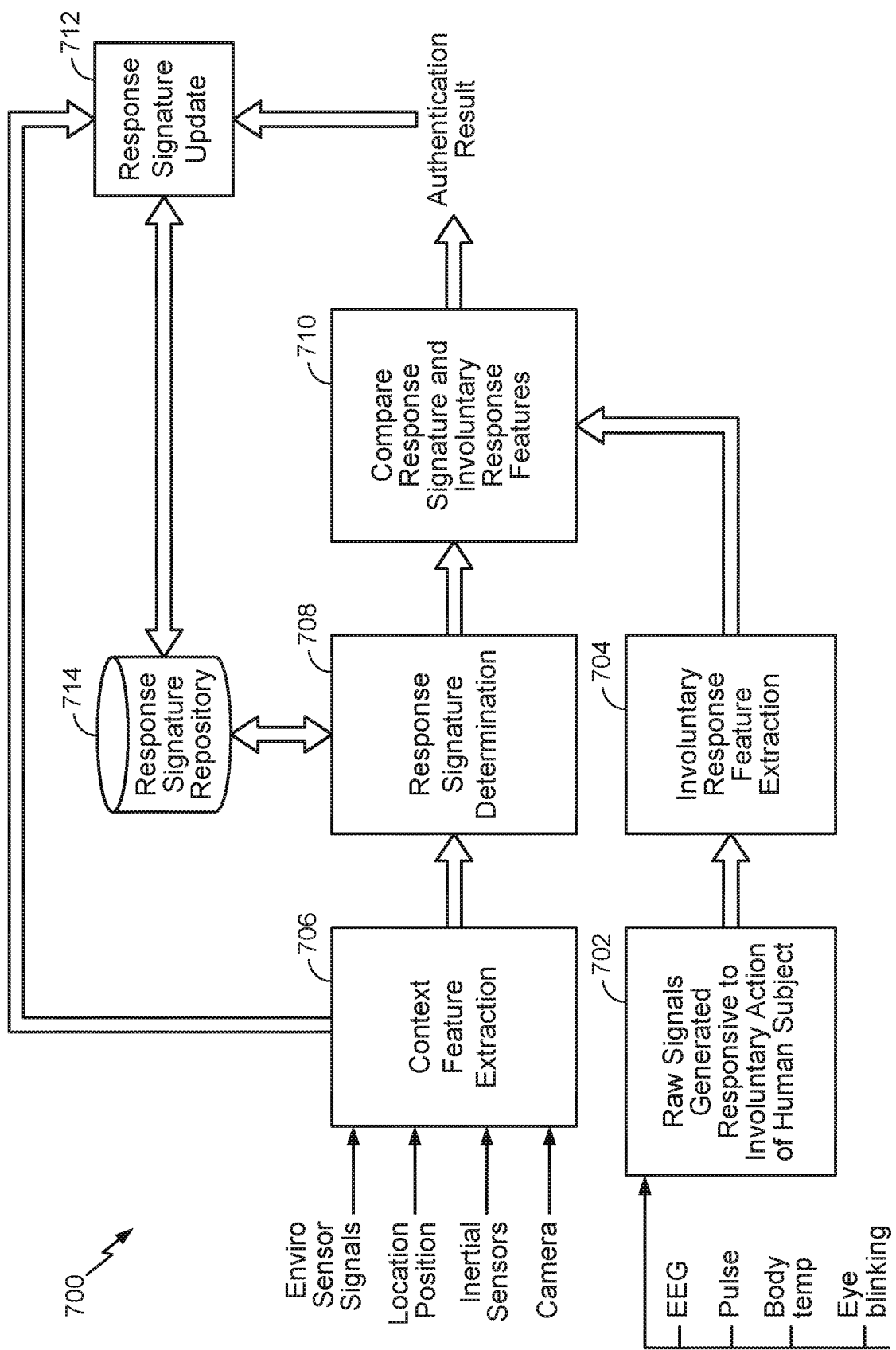
FIGS. 7 are 8 are flow diagrams of example processes to electronically authenticate an identity of a subject based, at lest in part, on a physical environment experienced by the subject.

FIGS. 7 are 8 are flow diagrams of processes to authenticate an identity of a human subject based, at least in part, on a physical environment experienced by such a human subject. In particular implementations of process 700 shown in FIG. 7, all or portions of process 700 may be performed by a computing device co-located with a human subject (e.g., goggles and/or glasses 506 co-located with human subject 500 and/or computing device 600). In other implementations, execution of portions of process 700 may be shared between or among a computing device co-located with a human subject and one or more devices remote from the computing device co-located with the human subject (e.g., shared between or among goggles and/or glasses 506 and/or computing device 600, and remote computing device(s) 502).

According to an embodiment, block 710 may determine an authentication result such as, for example, a determination of whether an identity of a human subject is that of a particular unique individual. In one implementation, such a determination may be provided in the form of a binary result. Such a binary result may comprise a determination that an identity of a human subject is or is not an identity of a particular unique individual. In another implementation, such a determination may be in the form of a likelihood or probability (e.g., a numerical likelihood or probability that an identity of a human a human subject is an identity of a particular unique individual). It should be understood, however, that these are merely examples of how a determination of an authentication result may be provided, and that claimed subject matter is not limited in this respect.

According to an embodiment, block 710 may compare a response signature with one or more involuntary response features to determine an authentication result. In an implementation, a response signature determined at block 708 may be indicative of one or more involuntary responses expected by a particular unique individual exposed to particular environmental stimuli. For example, a response signature determined at block 708 may be indicative of one or more involuntary responses expected by a particular unique individual if such a particular unique individual is exposed to certain environmental stimuli measured and/or detected based, at least in part, on signals from devices co-located with a human subject (e.g., environmental sensors, inertial sensors, camera, location determination devices).

According to an embodiment, a response signature repository 714 may electronically store (e.g., in a memory and/or non-transitory storage medium) signatures representative of expected involuntary responses by a particular unique individual to particular environmental stimuli. For example, response signature repository 714 may store signatures representative of expected involuntary responses which are measurable and/or detectable from devices co-located with a human subject such as sensors positioned on particular locations of a scalp to measure and/or detect brain signals (e.g., as shown in FIG. 2B), and/or sensors capable of detecting other involuntary responses such as, for example, a heart rate and/or heartbeat monitor, blood pressure monitor perspiration monitor, body thermometer, sensors capable of detection eye movement, pupillary response and/or blinking (e.g., eye tracker) or sensor capable of obtaining MEG scans, or any combination thereof, as discussed above. In one implementation, a neural network may identify a phenomenon that a human subject is currently observing (e.g., particular objects being viewed and/or particular sounds being heard). A neural network may further determine a probability and/or likelihood that the human subject is actually observing the identified phenomenon (e.g., probability that human subject is actually viewing an identified object and/or hearing a particular sound (e.g., sound generated by a particular source)). Such an identified phenomenon being observed (and associated probability that a human subject (e.g., particular unique individual) is indeed observing the identified phenomenon), may then be used to determine and/or select a process for determining an expected response to observing the identified phenomenon in the future. Subsequently, a neural network may compare expected and actual responses by a human subject (e.g., a particular unique individual) to observing the identified phenomenon and, if appropriate, update the process for determining an expected response to observing the identified phenomenon. In one alternative implementation, a neural network may be provided with attributes of the identified phenomenon (e.g., image of object and/or sound) and then generate an expected involuntary response (e.g., by a particular unique individual). The actual and generated (expected) involuntary response may then be compared for use in training the neural network. In another alternative implementation, an involuntary response may be used by a neural network to identify a class of observable phenomena that generate particular response(s) by a particular unique individual. A neural network may then determine a particular phenomenon that the particular unique individual is observing based, at least in part, on a comparison of an involuntary response by the particular unique individual to responses expected from a observing a predefined class of phenomena.

In an implementation, involuntary response features extracted at block 704 may be indicative of one or more involuntary responses of a human subject (to environmental stimuli) observed based, at least in part, on biometric response signals from devices co-located with a human subject such as sensors positioned on particular locations of a scalp to observe brain signals (e.g., as shown in FIG. 2B) and/or sensors to observe other involuntary responses of a human subject such as, for example, a heart rate and/or heartbeat monitor, perspiration monitor, body thermometer, sensors enabling MEG scans sensors capable of detection and/or tracking eye movement, pupillary response and/or blinking, as discussed above.

According to an embodiment, block 710 may determine an authentication result D according to expression (3) as follows:

$$D=F[RS(\theta|CF),IR(S)], \quad (3)$$

where:
RS($\theta$|CF) is a response signature characterizing an expected response by a particular unique individual $\theta$ to environmental stimuli characterized by context features CF; and
IR(S) comprises one or more features characterizing an observed involuntary response by a human subject to environmental stimuli based on signal observations S (e.g., observations of biometric response signals from devices co-located with a human subject).

In a particular implementation, RS($\theta$|CF) and IR(S) may be expressed as vectors and/or arrays of values determined by blocks 708 and 704, respectively. Also, as pointed above, authentication result D may take the form of a binary result and/or a likelihood and/or probability value. In one example scenario, context features CF may comprise, among other things, recognition in a camera image of an object of particular significance to particular unique individual $\theta$ such as, for example, a spouse, loved one, family member, pet, object and/or sound eliciting a strong response in a human subject, etc. while S may comprise brain signals detected at a BCI. Here, RS($\theta$|CF) may comprise features of a P300 brain signal that may be expected from particular unique individual $\theta$ responsive to a presence of such an object of particular significance to particular unique individual $\theta$. In particular implementations, one or more aspects of blocks 702, 704, 706 and/or 708 may be implemented as a neural network trained to extract involuntary response features from raw signals for determination of IR(S) and/or extract context features for determination of RS($\theta$|CF).

In one particular implementation where D takes the form of a binary result (e.g., wherein D=1 if an identity of a human subject is to be authenticated as an identity of $\theta$ and D=0 if an identity of a human subject is not to be authenticated as an identity of $\theta$), operation F may be implemented as a Bayesian detector according to expression (4) as follows:

$$D=1, \text{ if } \frac{P[RS(\theta|CF), IR(S)|HS=\theta]}{P[RS(\theta|CF), IR(S)|HS\neq\theta]} \geq \frac{P(HS\neq\theta)(U_{11}-U_{21})}{P(HS=\theta)(U_{22}-U_{12})} \quad (4)$$

-continued
$$D=0, \text{ if } \frac{P[RS(\theta|CF), IR(S)|HS=\theta]}{P[RS(\theta|CF), IR(S)|HS\neq\theta]} < \frac{P(HS\neq\theta)(U_{11}-U_{21})}{P(HS=\theta)(U_{22}-U_{12})},$$

Where:
P[RS($\theta$|CF), IR(S)|HS=$\theta$] is a probability of observing RS($\theta$|CF) and IR(S) if an identity of human subject HS is the identity of particular unique individual $\theta$;
P[RS($\theta$|CF), IR(S)|HS$\neq\theta$] is a probability of observing RS($\theta$|CF) and IR(S) if an identity of human subject HS is not the identity of particular unique individual $\theta$;
P(HS=$\theta$) is an a priori probability that an identity of human subject HS is the identity of particular unique individual $\theta$;
P(HS$\neq\theta$) is an a priori probability that an identity of human subject HS is not the identity of particular unique individual $\theta$;
$U_{11}$ is a utility of not authenticating identity of HS as identity of $\theta$ if identity of HS is not the identity of $\theta$;
$U_{12}$ is a utility of not authenticating identity of HS as identity of $\theta$ if identity of HS is the identity of $\theta$;
$U_{21}$ is a utility of authenticating identity of HS as identity of $\theta$ if identity of HS is not the identity of $\theta$; and
$U_{22}$ is a utility of authenticating identity of HS as identity of $\theta$ if identity of HS is the identity of $\theta$.

In an alternative implementation, a result D may be computed using a neural network trained to process raw signals by sensors generated responsive, at least in part, to involuntary action of a human subject and/or signals generated by sensors and/or devices characterizing a context and/or environment. Here, features of a neural network may be trained based, at least in part, on comparisons of actual observed involuntary responses by a particular unique to expected responses by the particular unique individual.

According to an embodiment, response signatures for a particular unique individual maintained in signature repository 714 may be continually updated by block 712 as part of a training operation based, at least in part, on an authentication result provided by block 710 and context features determined at block 706 based, at least in part, on observations based, at least in part, on signals from devices co-located with a human subject (e.g., environmental sensors, inertial sensors, camera, location determination devices). In one implementation, block 712 may be implemented, at least in part, by a neural network maintained by a neural network processor, central processing unit (e.g., general-purpose/application processor 611) and/or graphics processing unit. For example, a neural network hosted on a local device (e.g., goggles and/or glasses 506, mobile phone, etc.) or hosted on a remote computing platform (e.g., a remote computing platform 502) may be trained as discussed herein. In particular implementations, a neural network hosted on a local device may reduce securing risks (e.g., from hacking). In an embodiment, block 712 may update one or more response signatures stored in response signature repository 714 according to operation H as shown in expression (5) as follows:

$$\widehat{RS}(\theta|\overline{CF})=H[RS(\theta|\overline{CF}),IR(S),CF,D], \quad (5)$$

where:
$\widehat{RS}(\theta|\overline{CF})$ is a response signature for an expected response by particular unique individual $\theta$ to particular environmental stimuli context features CF updated based on current observations of environmental stimuli characterized by context features CF and current authentication result D that is to be maintained in response signature repository 714.

Continuing with the example above in which context features CF comprise recognition in a camera image of an object of particular significance to particular unique individual θ and RS(θ|CF) comprises features of a detectable and/or measurable response (e.g., P300 brain signal, eye movement, pupillary response, pulse, heart rate and/or heartbeat, blood pressure, body temperature, eye blinking, etc., or any combination thereof) that may be expected from particular unique individual θ responsive to a presence of such an object of particular significance to particular unique individual θ, CF may be updated as $\overline{CF}$ to further include a location context such as a location of a home or place of employment of particular unique individual θ. Furthermore, operation H may update RS(θ|$\overline{CF}$) as $\widehat{RS}$(θ|$\overline{CF}$) to further include some additional observation of an involuntary response by particular unique individual θ (e.g., involuntary response as measured by body sensors 662) to a presence of an object of particular significance to particular unique individual θ while at a particular location (e.g., home or place of employment of particular unique individual θ).

As pointed out above, execution of portions of process 700 may be shared between or among a computing device co-located with a human subject and one or more devices remote from such a computing device co-located with such a human subject (e.g., shared between or among goggles and/or glasses 506 and/or computing device 600, and remote computing device(s) 502). This may be enabled at least in part, by exchange of messages in a communication medium (e.g., wireless communication link 518). In one particular implementation, blocks 704 and 706 may be performed by a computing device co-located with a human subject while blocks 710, 712 and 714 may be performed by one or more computing devices remote from such a human subject. In an alternative implementation, blocks 704 and 706 may also be performed (in addition to blocks 710, 712 and 714) by one or more computing devices remote from a human subject. In this alternative implementation, a computing device co-located with a human subject may transmit to one or more remote computing devices messages containing measurements of raw signals generated by sensors (e.g., measurements collected at body sensors 662 and/or environmental sensors 660) and a location context to enable one or more remote computing devices to execute blocks 704, 706, 708, 710 and 712.

Figure 8:
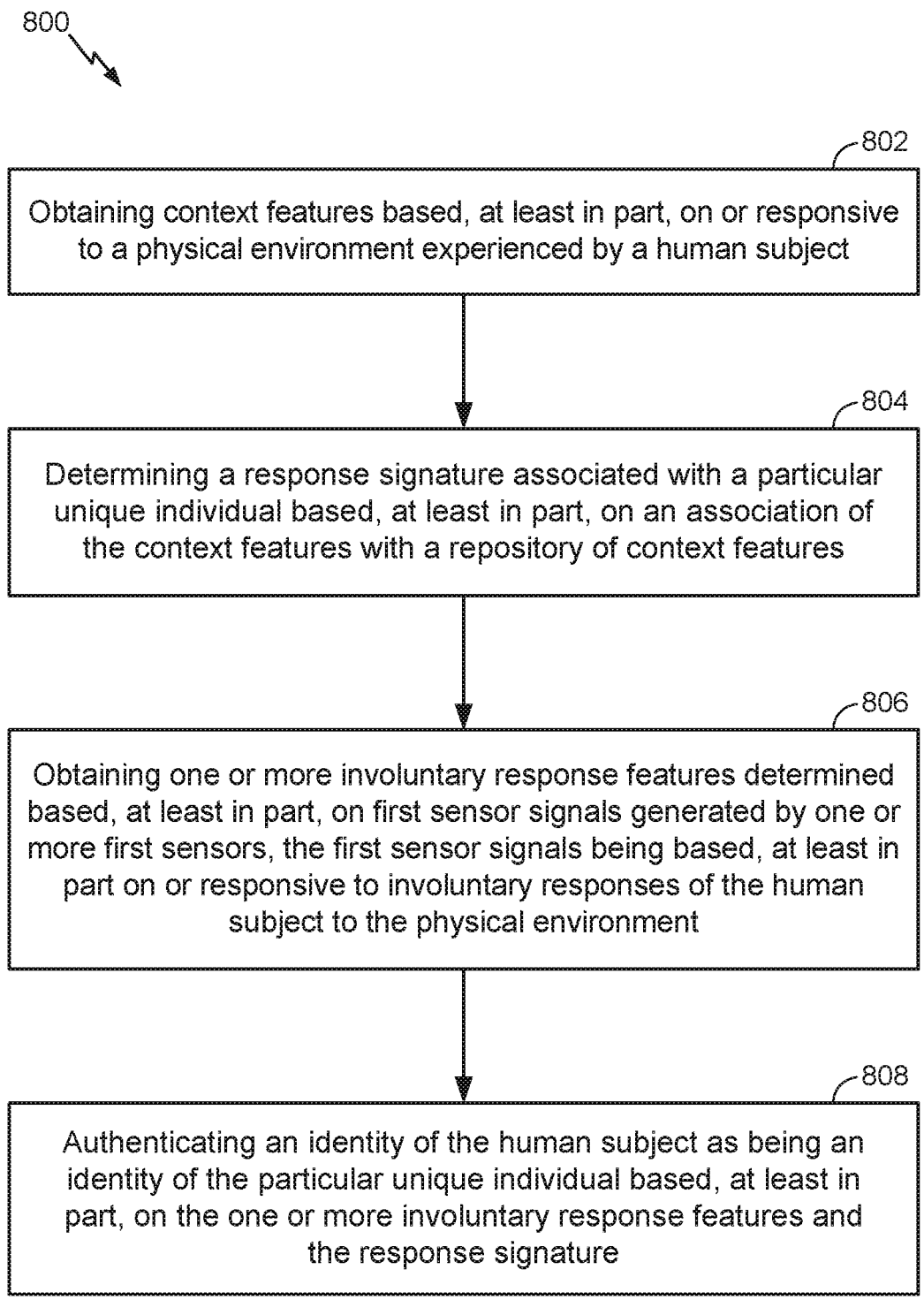

According to an embodiment, process 800 shown in FIG. 8 may be performed by a computing device as part of an implementation of an authentication process such as an authentication process 700 described above. In one particular implementation, all or portions of actions of process 800 may be performed by remote computing device(s) 502. In another particular implementation, all or portions of actions of process 800 may be performed by computing device 600 shown in FIG. 6. It should be noted that information acquired or produced, such as, for example, input signals, output signals, operations, results, etc. associated with example process 800 may be represented via one or more digital signals. It should also be appreciated that even though one or more operations are illustrated or described concurrently or with respect to a certain sequence, other sequences or concurrent operations may be employed. In addition, although the description below references particular aspects and/or features illustrated in certain other figures, one or more operations may be performed with other aspects and/or features. Thus, example process may, for example, begin at block 802 to comprise obtaining context features based, at least in part, on or responsive to a physical environment experienced by a subject. In this context, "context features" as referred to herein comprises one or more values and/or parameters indicative and/or descriptive of at least one aspect of a physical environment experienced by a subject. In an example implementation, block 802 may comprise obtaining context features at block 706 based, at least in part, on images obtained from camera 664 and/or observations of signals generated by environmental sensors 660 and/or inertial sensors 661 as described above. For example, a context feature may comprise recognition of an object in a camera image that is of particular significance to a particular unique individual (e.g., spouse, loved one or family member of the particular unique individual). It should be understood, however, that this is merely an example of a context feature, and that claimed subject matter is not limited in this respect.

In one particular implementation, one or more aspects of block 802 may be performed, at least in part, by a neural network. For example, a neural network may determine a state of a subject as being agitated, sick (e.g., with a cold or influenza), rested, tired, etc., based, at least in part, on observations of the subject (e.g., observations of P300 brain signal, phenomena detectable/measurable by a MEG scan, heartbeat, eye movement, pupillary response, pulse, blood pressure, body temperature or eye blinking, etc., or any combination thereof based, at least in part, on sensor signals) and/or other inputs. The neural network may then determine one or more context features of block 802 based, at least in part, on the determined state of the subject.

Block 804 may comprise determining a response signature associated with a particular unique individual based, at least in part, on context features determined at block 802. In this context, a "response feature" as referred to herein means one or more values and/or parameters indicative and/or descriptive of at least one aspect of a possible involuntary response by a human subject to a sensory stimulus. For example, a response signature may comprise detectable features of an expected involuntary response (e.g., P300 brain signal, phenomena detectable/measurable by a MEG scan, heartbeat, eye movement, pupillary response, pulse, blood pressure, body temperature or eye blinking, etc., or any combination thereof) detected in a human subject. Another response signature may comprise expected features of signals generated by one or more of body sensors 662. It should be understood, however, that this is merely an example of a response signature, and that claimed subject matter is not limited in this respect.

Block 804 may comprise a determination of a response signature based, at least in part, on an association of context features determined in block 802 with a repository of response signatures. In this context, a "repository of response signatures" as referred to herein means parameters and/or values maintained in a non-transitory storage medium to express response signatures organized according to detectable features of an environment (e.g., possible context features). In an example implementation, block 804 may comprise access by block 708 of response signature repository 714 to determine a response signature RS(θ|CF) for particular unique individual θ based, at least in part, on context features CF determined at block 706. Alternatively, as described herein, block 804 may comprise training a neural network processing device to generate a response signature RS(θ|CF) comprising signals indicative and/or representative of an expected response by a subject in the presence of detectable features of an environment.

According to an embodiment, one or more aspects of block 804 may be performed, at least in part, by a neural network. For example, one or more features of a neural network may be trained over time based, at least in part, on observations of responses by the particular unique individual to sensory stimuli over time (e.g., observations of responses by the particular unique individual to a physical environment over time). For example, based, at least in part, on sensor signals, the neural network may observe aspects of a subject believed with high confidence to the particular unique individual. Such observed aspects may include, for example, P300 brain signal, phenomena detectable/measurable by a MEG scan, heartbeat, eye movement, pupillary response, pulse, blood pressure, body temperature or eye blinking, etc., or any combination thereof. Block 804 may determine a response signature based, at least in part, on one or more of the trained features of the neural network.

Block 806 may comprise obtaining one or more involuntary response features based, at least in part, on observations of signals generated by devices co-located with a human subject to monitor involuntary responses of such a human subject to environmental stimuli. In this context, an "involuntary response feature" as referred to herein means one or more values and/or parameters indicative and/or descriptive of at least one aspect of an involuntary response by a human subject to a sensory stimulus that has been detected and/or measured. In a particular example, an involuntary response feature may comprise a detection of a detectable and/or measurable response (e.g., P300 brain signal, phenomena detectable/measurable by a MEG scan, heartbeat, eye movement, pupillary response, pulse, blood pressure, body temperature or eye blinking, etc., or any combination thereof) based, at least in part, on brain signals measured and/or detected at sensors placed on a scalp of a human subject (e.g., as shown in FIG. 2B). Another involuntary response feature may comprise detection of features in signals generated by one or more of body sensors 662. It should be understood, however, that this is merely an example of an involuntary response feature, and that claimed subject matter is not limited in this respect. In an example implementation, block 806 may comprise obtaining one or more involuntary response features IR(S) at block 704 which are based, at least in part, on observations of raw signals generated by body sensors 662 based, at least in part, on or responsive to physiological processes of a human subject (e.g., brain signals, pulse, blood pressure, pupillary response, body temperature, eye blinking, etc.). For example, a response signature may comprise detectable features of an expected P300 brain signal detected in a human subject. It should be understood, however, that this is merely an example of a response feature, and that claimed subject matter is not limited in this respect. According to an embodiment, it may be observed that different involuntary physiological responses by a subject to a physical environment may be probabilistically correlated (e.g., positively or negatively correlated). In a particular implementation, block 806 may determine one or more involuntary response features based, at least in part, on an application of a multivariable probabilistic model to a first observed involuntary response by the subject to the physical environment and at least a second observed involuntary response by the subject to the physical environment comprising an observed P300 brain signal, eye movement, eye blinking, heart rate, pupillary response, body temperature or blood pressure, or any combination thereof.

Block 808 may comprise authentication of an identity of a human subject as being an identity of a particular unique individual based, at least in part, on one or more involuntary response features obtained at block 806 and a response signature obtained at block 804. For example, block 808 may comprise operations to be performed at block 710 to determine an authentication result D feature according to expression (3) and/or expression (4) as discussed above. It should be understood, however, that this is merely an example of how an authentication result may be determined based, at least in part, on one or more involuntary response features and a response signature, and claimed subject matter is not limited in this respect.

According to an embodiment, an authentication result D determined at block 808 may be further used to update a signature repository (e.g., signature repository 714) according to expression (5) and/or train a neural network and/or one or more fully connected layers of a neural network, for example. Additionally, determination of an authentication result at block 808 may further enable determination of whether a particular individual is to be authorized to receive a particular level of service or to access a device as discussed above.

As may be observed, one or more particular implementations of processes 700 and 800 may enable real-time authentication of an identity of a human subject based, at least in part, on observations of involuntary processes of such a human subject (e.g., based on signals from sensors monitoring such involuntary processes) and observations of an environment experienced by such a human subject. This may be accomplished at least in part by processing and combining of sensors signals indicative of observations of involuntary processes of such a human subject and sensor signals indicative of observations a physical environment being experienced by such a human subject in a unique manner as described above. This may reduce or eliminate reliance on voluntary actions by a human subject (e.g., entering a password to a keypad, speaking, interacting with a biometric sensing device, etc.) in a process to authenticate an identity of such a human subject.

In one particular scenario, a physical environment may not be sufficiently varied and/or distinct to enable block 802 to obtain reliable context features based, at least in part on observations of a human subject. Here, in lieu of such a physical environment, an artificial stimulus (e.g., images, sounds, odors, lighting, ambient temperature, humidity, etc.) may be applied the human subject so that observable responses by the human subject to the artificial stimulus enable obtaining context features.

In another embodiment, based, at least in part, on context features obtained at block 802 and involuntary response features obtained at block 806, block 808 may not be able to reliably authenticate a subject based, at least in part, on the context features and the response features. Here, a prompt (e.g., visual or auditory prompt) may be provided to the human subject to provide a password (or other voluntary response) in lieu of a reliable authentication at block 808.

In the context of the present patent application, the term "connection," the term "component" and/or similar terms are intended to be physical, but are not necessarily always tangible. Whether or not these terms refer to tangible subject matter, thus, may vary in a particular context of usage. As an example, a tangible connection and/or tangible connection path may be made, such as by a tangible, electrical connection, such as an electrically conductive path comprising metal or other conductor, that is able to conduct electrical current between two tangible components. Likewise, a tangible connection path may be at least partially affected and/or controlled, such that, as is typical, a tangible connection path may be open or closed, at times resulting from influence of one or more externally derived signals, such as external currents and/or voltages, such as for an electrical switch. Non-limiting illustrations of an electrical switch include a transistor, a diode, etc. However, a "connection" and/or "component," in a particular context of usage, likewise, although physical, can also be non-tangible, such as a connection between a client and a server over a network, particularly a wireless network, which generally refers to the ability for the client and server to transmit, receive, and/or exchange communications, as discussed in more detail later.

In a particular context of usage, such as a particular context in which tangible components are being discussed, therefore, the terms "coupled" and "connected" are used in a manner so that the terms are not synonymous. Similar terms may also be used in a manner in which a similar intention is exhibited. Thus, "connected" is used to indicate that two or more tangible components and/or the like, for example, are tangibly in direct physical contact. Thus, using the previous example, two tangible components that are electrically connected are physically connected via a tangible electrical connection, as previously discussed. However, "coupled," is used to mean that potentially two or more tangible components are tangibly in direct physical contact. Nonetheless, "coupled" is also used to mean that two or more tangible components and/or the like are not necessarily tangibly in direct physical contact, but are able to co-operate, liaise, and/or interact, such as, for example, by being "optically coupled." Likewise, the term "coupled" is also understood to mean indirectly connected. It is further noted, in the context of the present patent application, since memory, such as a memory component and/or memory states, is intended to be non-transitory, the term physical, at least if used in relation to memory necessarily implies that such memory components and/or memory states, continuing with the example, are tangible.

Unless otherwise indicated, in the context of the present patent application, the term "or" if used to associate a list, such as A, B, or C, is intended to mean A, B, and C, here used in the inclusive sense, as well as A, B, or C, here used in the exclusive sense. With this understanding, "and" is used in the inclusive sense and intended to mean A, B, and C; whereas "and/or" can be used in an abundance of caution to make clear that all of the foregoing meanings are intended, although such usage is not required. In addition, the term "one or more" and/or similar terms is used to describe any feature, structure, characteristic, and/or the like in the singular, "and/or" is also used to describe a plurality and/or some other combination of features, structures, characteristics, and/or the like. Likewise, the term "based on" and/or similar terms are understood as not necessarily intending to convey an exhaustive list of factors, but to allow for existence of additional factors not necessarily expressly described.

Furthermore, it is intended, for a situation that relates to implementation of claimed subject matter and is subject to testing, measurement, and/or specification regarding degree, that the particular situation be understood in the following manner. As an example, in a given situation, assume a value of a physical property is to be measured. If alternatively reasonable approaches to testing, measurement, and/or specification regarding degree, at least with respect to the property, continuing with the example, is reasonably likely to occur to one of ordinary skill, at least for implementation purposes, claimed subject matter is intended to cover those alternatively reasonable approaches unless otherwise expressly indicated. As an example, if a plot of measurements over a region is produced and implementation of claimed subject matter refers to employing a measurement of slope over the region, but a variety of reasonable and alternative techniques to estimate the slope over that region exist, claimed subject matter is intended to cover those reasonable alternative techniques unless otherwise expressly indicated.

To the extent claimed subject matter is related to one or more particular measurements, such as with regard to physical manifestations capable of being measured physically, such as, without limit, temperature, pressure, voltage, current, electromagnetic radiation, etc., it is believed that claimed subject matter does not fall with the abstract idea judicial exception to statutory subject matter. Rather, it is asserted, that physical measurements are not mental steps and, likewise, are not abstract ideas.

It is noted, nonetheless, that a typical measurement model employed is that one or more measurements may respectively comprise a sum of at least two components. Thus, for a given measurement, for example, one component may comprise a deterministic component, which in an ideal sense, may comprise a physical value (e.g., sought via one or more measurements), often in the form of one or more signals, signal samples and/or states, and one component may comprise a random component, which may have a variety of sources that may be challenging to quantify. At times, for example, lack of measurement precision may affect a given measurement. Thus, for claimed subject matter, a statistical or stochastic model may be used in addition to a deterministic model as an approach to identification and/or prediction regarding one or more measurement values that may relate to claimed subject matter.

For example, a relatively large number of measurements may be collected to better estimate a deterministic component. Likewise, if measurements vary, which may typically occur, it may be that some portion of a variance may be explained as a deterministic component, while some portion of a variance may be explained as a random component. Typically, it is desirable to have stochastic variance associated with measurements be relatively small, if feasible. That is, typically, it may be preferable to be able to account for a reasonable portion of measurement variation in a deterministic manner, rather than a stochastic matter as an aid to identification and/or predictability.

Along these lines, a variety of techniques have come into use so that one or more measurements may be processed to better estimate an underlying deterministic component, as well as to estimate potentially random components. These techniques, of course, may vary with details surrounding a given situation. Typically, however, more complex problems may involve use of more complex techniques. In this regard, as alluded to above, one or more measurements of physical manifestations may be modelled deterministically and/or stochastically. Employing a model permits collected measurements to potentially be identified and/or processed, and/or potentially permits estimation and/or prediction of an underlying deterministic component, for example, with respect to later measurements to be taken. A given estimate may not be a perfect estimate; however, in general, it is expected that on average one or more estimates may better reflect an underlying deterministic component, for example, if random components that may be included in one or more obtained measurements, are considered. Practically speaking, of course, it is desirable to be able to generate, such as through estimation approaches, a physically meaningful model of processes affecting measurements to be taken.

In some situations, however, as indicated, potential influences may be complex. Therefore, seeking to understand appropriate factors to consider may be particularly challenging. In such situations, it is, therefore, not unusual to employ heuristics with respect to generating one or more estimates. Heuristics refers to use of experience related approaches that may reflect realized processes and/or realized results, such as with respect to use of historical measurements, for example. Heuristics, for example, may be employed in situations where more analytical approaches may be overly complex and/or nearly intractable. Thus, regarding claimed subject matter, an innovative feature may include, in an example embodiment, heuristics that may be employed, for example, to estimate and/or predict one or more measurements.

It is further noted that the terms "type" and/or "like," if used, such as with a feature, structure, characteristic, and/or the like, using "optical" or "electrical" as simple examples, means at least partially of and/or relating to the feature, structure, characteristic, and/or the like in such a way that presence of minor variations, even variations that might otherwise not be considered fully consistent with the feature, structure, characteristic, and/or the like, do not in general prevent the feature, structure, characteristic, and/or the like from being of a "type" and/or being "like," (such as being an "optical-type" or being "optical-like," for example) if the minor variations are sufficiently minor so that the feature, structure, characteristic, and/or the like would still be considered to be substantially present with such variations also present. Thus, continuing with this example, the terms optical-type and/or optical-like properties are necessarily intended to include optical properties. Likewise, the terms electrical-type and/or electrical-like properties, as another example, are necessarily intended to include electrical properties. It should be noted that the specification of the present patent application merely provides one or more illustrative examples and claimed subject matter is intended to not be limited to one or more illustrative examples; however, again, as has always been the case with respect to the specification of a patent application, particular context of description and/or usage provides helpful guidance regarding reasonable inferences to be drawn.

With advances in technology, it has become more typical to employ distributed computing and/or communication approaches in which portions of a process, such as signal processing of signal samples, for example, may be allocated among various devices, including one or more client devices and/or one or more server devices, via a computing and/or communications network, for example. A network may comprise two or more devices, such as network devices and/or computing devices, and/or may couple devices, such as network devices and/or computing devices, so that signal communications, such as in the form of signal packets and/or signal frames (e.g., comprising one or more signal samples), for example, may be exchanged, such as between a server device and/or a client device, as well as other types of devices, including between wired and/or wireless devices coupled via a wired and/or wireless network, for example.

In the context of the present patent application, the term network device refers to any device capable of communicating via and/or as part of a network and may comprise a computing device. While network devices may be capable of communicating signals (e.g., signal packets and/or frames), such as via a wired and/or wireless network, they may also be capable of performing operations associated with a computing device, such as arithmetic and/or logic operations, processing and/or storing operations (e.g., storing signal samples), such as in memory as tangible, physical memory states, and/or may, for example, operate as a server device and/or a client device in various embodiments. Network devices capable of operating as a server device, a client device and/or otherwise, may include, as examples, dedicated rack-mounted servers, desktop computers, laptop computers, set top boxes, tablets, netbooks, smart phones, wearable devices, integrated devices combining two or more features of the foregoing devices, and/or the like, or any combination thereof. As mentioned, signal packets and/or frames, for example, may be exchanged, such as between a server device and/or a client device, as well as other types of devices, including between wired and/or wireless devices coupled via a wired and/or wireless network, for example, or any combination thereof. It is noted that the terms, server, server device, server computing device, server computing platform and/or similar terms are used interchangeably. Similarly, the terms client, client device, client computing device, client computing platform and/or similar terms are also used interchangeably. While in some instances, for ease of description, these terms may be used in the singular, such as by referring to a "client device" or a "server device," the description is intended to encompass one or more client devices and/or one or more server devices, as appropriate. Along similar lines, references to a "database" are understood to mean, one or more databases and/or portions thereof, as appropriate.

It should be understood that for ease of description, a network device (also referred to as a networking device) may be embodied and/or described in terms of a computing device and vice-versa. However, it should further be understood that this description should in no way be construed so that claimed subject matter is limited to one embodiment, such as only a computing device and/or only a network device, but, instead, may be embodied as a variety of devices or combinations thereof, including, for example, one or more illustrative examples.

A network may also include now known, and/or to be later developed arrangements, derivatives, and/or improvements, including, for example, past, present and/or future mass storage, such as network attached storage (NAS), a storage area network (SAN), and/or other forms of device readable media, for example. A network may include a portion of the Internet, one or more local area networks (LANs), one or more wide area networks (WANs), wire-line type connections, wireless type connections, other connections, or any combination thereof. Thus, a network may be worldwide in scope and/or extent. Likewise, sub-networks, such as may employ differing architectures and/or may be substantially compliant and/or substantially compatible with differing protocols, such as network computing and/or communications protocols (e.g., network protocols), may interoperate within a larger network.

In the context of the present patent application, the term sub-network and/or similar terms, if used, for example, with respect to a network, refers to the network and/or a part thereof. Sub-networks may also comprise links, such as physical links, connecting and/or coupling nodes, so as to be capable to communicate signal packets and/or frames between devices of particular nodes, including via wired links, wireless links, or combinations thereof. Various types of devices, such as network devices and/or computing devices, may be made available so that device interoperability is enabled and/or, in at least some instances, may be transparent. In the context of the present patent application, the term "transparent," if used with respect to devices of a network, refers to devices communicating via the network in which the devices are able to communicate via one or more intermediate devices, such as one or more intermediate nodes, but without the communicating devices necessarily specifying the one or more intermediate nodes and/or the one or more intermediate devices of the one or more intermediate nodes and/or, thus, may include within the network the devices communicating via the one or more intermediate nodes and/or the one or more intermediate devices of the one or more intermediate nodes, but may engage in signal communications as if such intermediate nodes and/or intermediate devices are not necessarily involved. For example, a router may provide a link and/or connection between otherwise separate and/or independent LANs.

In the context of the present patent application, a "private network" refers to a particular, limited set of devices, such as network devices and/or computing devices, able to communicate with other devices, such as network devices and/or computing devices, in the particular, limited set, such as via signal packet and/or signal frame communications, for example, without a need for re-routing and/or redirecting signal communications. A private network may comprise a stand-alone network; however, a private network may also comprise a subset of a larger network, such as, for example, without limitation, all or a portion of the Internet. Thus, for example, a private network "in the cloud" may refer to a private network that comprises a subset of the Internet. Although signal packet and/or frame communications (e.g. signal communications) may employ intermediate devices of intermediate nodes to exchange signal packets and/or signal frames, those intermediate devices may not necessarily be included in the private network by not being a source or designated destination for one or more signal packets and/or signal frames, for example. It is understood in the context of the present patent application that a private network may direct outgoing signal communications to devices not in the private network, but devices outside the private network may not necessarily be able to direct inbound signal communications to devices included in the private network.

The Internet refers to a decentralized global network of interoperable networks that comply with the Internet Protocol (IP). It is noted that there are several versions of the Internet Protocol. The term Internet Protocol, IP, and/or similar terms are intended to refer to any version, now known and/or to be later developed. The Internet includes local area networks (LANs), wide area networks (WANs), wireless networks, and/or long haul public networks that, for example, may allow signal packets and/or frames to be communicated between LANs. The term World Wide Web (WWW or Web) and/or similar terms may also be used, although it refers to a part of the Internet that complies with the Hypertext Transfer Protocol (HTTP). For example, network devices may engage in an HTTP session through an exchange of appropriately substantially compatible and/or substantially compliant signal packets and/or frames. It is noted that there are several versions of the Hypertext Transfer Protocol. The term Hypertext Transfer Protocol, HTTP, and/or similar terms are intended to refer to any version, now known and/or to be later developed. It is likewise noted that in various places in this document substitution of the term Internet with the term World Wide Web ("Web") may be made without a significant departure in meaning and may, therefore, also be understood in that manner if the statement would remain correct with such a substitution.

The term electronic file and/or the term electronic document are used throughout this document to refer to a set of stored memory states and/or a set of physical signals associated in a manner so as to thereby at least logically form a file (e.g., electronic) and/or an electronic document. That is, it is not meant to implicitly reference a particular syntax, format and/or approach used, for example, with respect to a set of associated memory states and/or a set of associated physical signals. If a particular type of file storage format and/or syntax, for example, is intended, it is referenced expressly. It is further noted an association of memory states, for example, may be in a logical sense and not necessarily in a tangible, physical sense. Thus, although signal and/or state components of a file and/or an electronic document, for example, are to be associated logically, storage thereof, for example, may reside in one or more different places in a tangible, physical memory, in an embodiment.

A Hyper Text Markup Language ("HTML"), for example, may be utilized to specify digital content and/or to specify a format thereof, such as in the form of an electronic file and/or an electronic document, such as a Web page, Web site, etc., for example. An Extensible Markup Language ("XML") may also be utilized to specify digital content and/or to specify a format thereof, such as in the form of an electronic file and/or an electronic document, such as a Web page, Web site, etc., in an embodiment. Of course, HTML and/or XML are merely examples of "markup" languages, provided as non-limiting illustrations. Furthermore, HTML and/or XML are intended to refer to any version, now known and/or to be later developed, of these languages. Likewise, claimed subject matter are not intended to be limited to examples provided as illustrations, of course.

In the context of the present patent application, the terms "entry," "electronic entry," "document," "electronic document," "content,", "digital content," "item," and/or similar terms are meant to refer to signals and/or states in a physical format, such as a digital signal and/or digital state format, e.g., that may be perceived by a user if displayed, played, tactilely generated, etc. and/or otherwise executed by a device, such as a digital device, including, for example, a computing device, but otherwise might not necessarily be readily perceivable by humans (e.g., if in a digital format). Likewise, in the context of the present patent application, digital content provided to a user in a form so that the user is able to readily perceive the underlying content itself (e.g., content presented in a form consumable by a human, such as hearing audio, feeling tactile sensations and/or seeing images, as examples) is referred to, with respect to the user, as "consuming" digital content, "consumption" of digital content, "consumable" digital content and/or similar terms. For one or more embodiments, an electronic document and/or an electronic file may comprise a Web page of code (e.g., computer instructions) in a markup language executed or to be executed by a computing and/or networking device, for example. In another embodiment, an electronic document and/or electronic file may comprise a portion and/or a region of a Web page. However, claimed subject matter is not intended to be limited in these respects.

Also, for one or more embodiments, an electronic document and/or electronic file may comprise a number of components. As previously indicated, in the context of the present patent application, a component is physical, but is not necessarily tangible. As an example, components with reference to an electronic document and/or electronic file, in one or more embodiments, may comprise text, for example, in the form of physical signals and/or physical states (e.g., capable of being physically displayed). Typically, memory states, for example, comprise tangible components, whereas physical signals are not necessarily tangible, although signals may become (e.g., be made) tangible, such as if appearing on a tangible display, for example, as is not uncommon. Also, for one or more embodiments, components with reference to an electronic document and/or electronic file may comprise a graphical object, such as, for example, an image, such as a digital image, and/or sub-objects, including attributes thereof, which, again, comprise physical signals and/or physical states (e.g., capable of being tangibly displayed). In an embodiment, digital content may comprise, for example, text, images, audio, video, and/or other types of electronic documents and/or electronic files, including portions thereof, for example.

Also, in the context of the present patent application, the term "parameters" (e.g., one or more parameters), "values" (e.g., one or more values), "symbols" (e.g., one or more symbols) "bits" (e.g., one or more bits), "elements" (e.g., one or more elements), "characters" (e.g., one or more characters), "numbers" (e.g., one or more numbers), "numerals" (e.g., one or more numerals) or "measurements" (e.g., one or more measurements) refer to material descriptive of a collection of signals, such as in one or more electronic documents and/or electronic files, and exist in the form of physical signals and/or physical states, such as memory states. For example, one or more parameters, values, symbols, bits, elements, characters, numbers, numerals or measurements, such as referring to one or more aspects of an electronic document and/or an electronic file comprising an image, may include, as examples, time of day at which an image was captured, latitude and longitude of an image capture device, such as a camera, for example, etc. In another example, one or more parameters, values, symbols, bits, elements, characters, numbers, numerals or measurements, relevant to digital content, such as digital content comprising a technical article, as an example, may include one or more authors, for example. Claimed subject matter is intended to embrace meaningful, descriptive parameters, values, symbols, bits, elements, characters, numbers, numerals or measurements in any format, so long as the one or more parameters, values, symbols, bits, elements, characters, numbers, numerals or measurements comprise physical signals and/or states, which may include, as parameter, value, symbol bits, elements, characters, numbers, numerals or measurements examples, collection name (e.g., electronic file and/or electronic document identifier name), technique of creation, purpose of creation, time and date of creation, logical path if stored, coding formats (e.g., type of computer instructions, such as a markup language) and/or standards and/or specifications used so as to be protocol compliant (e.g., meaning substantially compliant and/or substantially compatible) for one or more uses, and so forth.

Signal packet communications and/or signal frame communications, also referred to as signal packet transmissions and/or signal frame transmissions (or merely "signal packets" or "signal frames"), may be communicated between nodes of a network, where a node may comprise one or more network devices and/or one or more computing devices, for example. As an illustrative example, but without limitation, a node may comprise one or more sites employing a local network address, such as in a local network address space. Likewise, a device, such as a network device and/or a computing device, may be associated with that node. It is also noted that in the context of this patent application, the term "transmission" is intended as another term for a type of signal communication that may occur in any one of a variety of situations. Thus, it is not intended to imply a particular directionality of communication and/or a particular initiating end of a communication path for the "transmission" communication. For example, the mere use of the term in and of itself is not intended, in the context of the present patent application, to have particular implications with respect to the one or more signals being communicated, such as, for example, whether the signals are being communicated "to" a particular device, whether the signals are being communicated "from" a particular device, and/or regarding which end of a communication path may be initiating communication, such as, for example, in a "push type" of signal transfer or in a "pull type" of signal transfer. In the context of the present patent application, push and/or pull type signal transfers are distinguished by which end of a communications path initiates signal transfer.

Thus, a signal packet and/or frame may, as an example, be communicated via a communication channel and/or a communication path, such as comprising a portion of the Internet and/or the Web, from a site via an access node coupled to the Internet or vice-versa. Likewise, a signal packet and/or frame may be forwarded via network nodes to a target site coupled to a local network, for example. A signal packet and/or frame communicated via the Internet and/or the Web, for example, may be routed via a path, such as either being "pushed" or "pulled," comprising one or more gateways, servers, etc. that may, for example, route a signal packet and/or frame, such as, for example, substantially in accordance with a target and/or destination address and availability of a network path of network nodes to the target and/or destination address. Although the Internet and/or the Web comprise a network of interoperable networks, not all of those interoperable networks are necessarily available and/or accessible to the public.

In the context of the particular patent application, a network protocol, such as for communicating between devices of a network, may be characterized, at least in part, substantially in accordance with a layered description, such as the so-called Open Systems Interconnection (OSI) seven layer type of approach and/or description. A network computing and/or communications protocol (also referred to as a network protocol) refers to a set of signaling conventions, such as for communication transmissions, for example, as may take place between and/or among devices in a network. In the context of the present patent application, the term "between" and/or similar terms are understood to include "among" if appropriate for the particular usage and vice-versa. Likewise, in the context of the present patent application, the terms "compatible with," "comply with" and/or similar terms are understood to respectively include substantial compatibility and/or substantial compliance.

A network protocol, such as protocols characterized substantially in accordance with the aforementioned OSI description, has several layers. These layers are referred to as a network stack. Various types of communications (e.g., transmissions), such as network communications, may occur across various layers. A lowest level layer in a network stack, such as the so-called physical layer, may characterize how symbols (e.g., bits and/or bytes) are communicated as one or more signals (and/or signal samples) via a physical medium (e.g., twisted pair copper wire, coaxial cable, fiber optic cable, wireless air interface, combinations thereof, etc.). Progressing to higher-level layers in a network protocol stack, additional operations and/or features may be available via engaging in communications that are substantially compatible and/or substantially compliant with a particular network protocol at these higher-level layers. For example, higher-level layers of a network protocol may, for example, affect device permissions, user permissions, etc.

A network and/or sub-network, in an embodiment, may communicate via signal packets and/or signal frames, such via participating digital devices and may be substantially compliant and/or substantially compatible with, but is not limited to, now known and/or to be developed, versions of any of the following network protocol stacks: ARCNET, AppleTalk, ATM, Bluetooth®, DECnet, Ethernet, FDDI, Frame Relay, HIPPI, IEEE 1394, IEEE 802.11, IEEE-488, Internet Protocol Suite, IPX, Myrinet, OSI Protocol Suite, QsNet, RS-232, SPX, System Network Architecture, Token Ring, USB, and/or X.25. A network and/or sub-network may employ, for example, a version, now known and/or later to be developed, of the following: TCP/IP, UDP, DECnet, NetBEUI, IPX, AppleTalk and/or the like. Versions of the Internet Protocol (IP) may include IPv4, IPv6, and/or other later to be developed versions.

Regarding aspects related to a network, including a communications and/or computing network, a wireless network may couple devices, including client devices, with the network. A wireless network may employ stand-alone, ad-hoc networks, mesh networks, Wireless LAN (WLAN) networks, cellular networks, and/or the like. A wireless network may further include a system of terminals, gateways, routers, and/or the like coupled by wireless radio links, and/or the like, which may move freely, randomly and/or organize themselves arbitrarily, such that network topology may change, at times even rapidly. A wireless network may further employ a plurality of network access technologies, including a version of Long Term Evolution (LTE), WLAN, Wireless Router (WR) mesh, 2nd, 3rd, or 4th generation (2G, 3G, or 4G) cellular technology and/or the like, whether currently known and/or to be later developed. Network access technologies may enable wide area coverage for devices, such as computing devices and/or network devices, with varying degrees of mobility, for example.

A network may enable radio frequency and/or other wireless type communications via a wireless network access technology and/or air interface, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth®, ultra-wideband (UWB), 802.11b/g/n, 802.11ad, 802.11ay and/or the like. A wireless network may include virtually any type of now known and/or to be developed wireless communication mechanism and/or wireless communications protocol by which signals may be communicated between devices, between networks, within a network, and/or the like, including the foregoing, of course.

Figure 9:
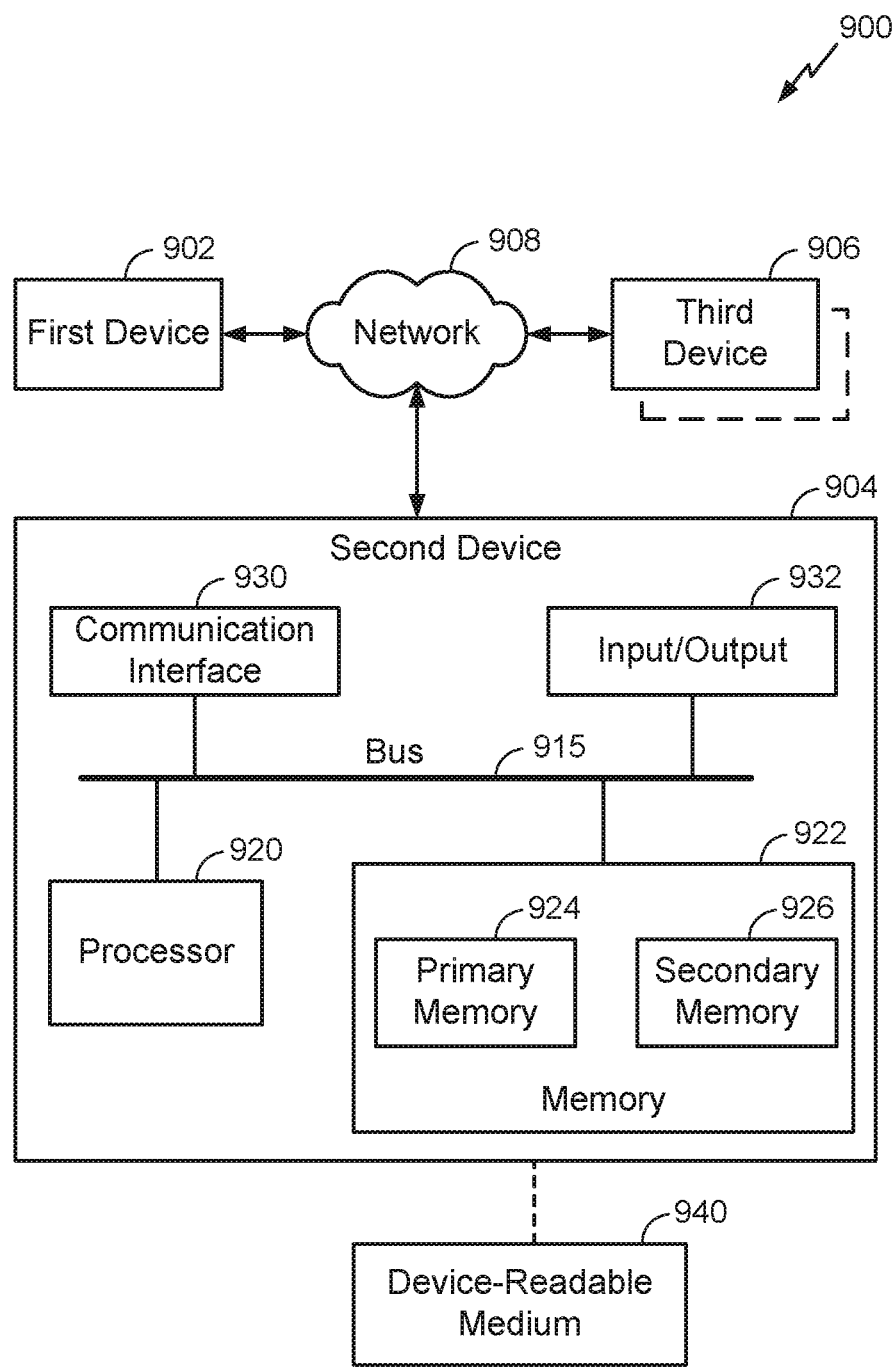
FIG. 9 is a schematic diagram illustrating an implementation of an example computing environment associated with a process to electronically authenticate an identity of a subject according to an embodiment.

In one example embodiment, as shown in FIG. 9, a system embodiment may comprise a local network (e.g., device 904 and medium 940) and/or another type of network, such as a computing and/or communications network. For purposes of illustration, therefore, FIG. 9 shows an embodiment 900 of a system that may be employed to implement either type or both types of networks. Network 908 may comprise one or more network connections, links, processes, services, applications, and/or resources to facilitate and/or support communications, such as an exchange of communication signals, for example, between a computing device, such as 902, and another computing device, such as 906, which may, for example, comprise one or more client computing devices and/or one or more server computing device. By way of example, but not limitation, network 908 may comprise wireless and/or wired communication links, telephone and/or telecommunications systems, Wi-Fi networks, Wi-MAX networks, the Internet, a local area network (LAN), a wide area network (WAN), or any combinations thereof.

Example devices in FIG. 9 may comprise features, for example, of a client computing device and/or a server computing device, in an embodiment. It is further noted that the term computing device, in general, whether employed as a client and/or as a server, or otherwise, refers at least to a processor and a memory connected by a communication bus. Likewise, in the context of the present patent application at least, this is understood to refer to sufficient structure within the meaning of 35 USC § 112 (f) so that it is specifically intended that 35 USC § 112 (f) not be implicated by use of the term "computing device" and/or similar terms; however, if it is determined, for some reason not immediately apparent, that the foregoing understanding cannot stand and that 35 USC § 112 (f), therefore, necessarily is implicated by the use of the term "computing device" and/or similar terms, then, it is intended, pursuant to that statutory section, that corresponding structure, material and/or acts for performing one or more functions be understood and be interpreted to be described at least in FIGS. 3, 4, 7 and 8 in the text associated with the foregoing figure(s) of the present patent application.

Referring now to FIG. 9, in an embodiment, first and third devices 902 and 906 may be capable of rendering a graphical user interface (GUI) for a network device and/or a computing device, for example, so that a user-operator may engage in system use. Device 904 may potentially serve a similar function in this illustration. Likewise, in FIG. 9, computing device 902 ('first device' in figure) may interface with computing device 904 ('second device' in figure), which may, for example, also comprise features of a client computing device and/or a server computing device, in an embodiment. Processor (e.g., processing device) 920 and memory 922, which may comprise primary memory 924 and secondary memory 926, may communicate by way of a communication bus 915, for example. The term "computing device," in the context of the present patent application, refers to a system and/or a device, such as a computing apparatus, that includes a capability to process (e.g., perform computations) and/or store digital content, such as electronic files, electronic documents, measurements, text, images, video, audio, etc. in the form of signals and/or states. Thus, a computing device, in the context of the present patent application, may comprise hardware, software, firmware, or any combination thereof (other than software per se). Computing device 904, as depicted in FIG. 9, is merely one example, and claimed subject matter is not limited in scope to this particular example.

For one or more embodiments, a device, such as a computing device and/or networking device, may comprise, for example, any of a wide range of digital electronic devices, including, but not limited to, desktop and/or notebook computers, high-definition televisions, digital versatile disc (DVD) and/or other optical disc players and/or recorders, game consoles, satellite television receivers, cellular telephones, tablet devices, wearable devices, personal digital assistants, mobile audio and/or video playback and/or recording devices, Internet of Things (IOT) type devices, or any combination of the foregoing. Further, unless specifically stated otherwise, a process as described, such as with reference to flow diagrams and/or otherwise, may also be executed and/or affected, in whole or in part, by a computing device and/or a network device. A device, such as a computing device and/or network device, may vary in terms of capabilities and/or features. Claimed subject matter is intended to cover a wide range of potential variations. For example, a device may include a numeric keypad and/or other display of limited functionality, such as a monochrome liquid crystal display (LCD) for displaying text, for example. In contrast, however, as another example, a web-enabled device may include a physical and/or a virtual keyboard, mass storage, one or more accelerometers, one or more gyroscopes, global positioning system (GPS) and/or other location-identifying type capability, and/or a display with a higher degree of functionality, such as a touch-sensitive color 2D or 3D display, for example.

As suggested previously, communications between a computing device and/or a network device and a wireless network may be in accordance with known and/or to be developed network protocols including, for example, global system for mobile communications (GSM), enhanced data rate for GSM evolution (EDGE), 802.11b/g/n/h, etc., and/or worldwide interoperability for microwave access (WIMAX). A computing device and/or a networking device may also have a subscriber identity module (SIM) card, which, for example, may comprise a detachable or embedded smart card that is able to store subscription content of a user, and/or is also able to store a contact list. It is noted, however, that a SIM card may also be electronic, meaning that is may simply be stored in a particular location in memory of the computing and/or networking device. A user may own the computing device and/or network device or may otherwise be a user, such as a primary user, for example. A device may be assigned an address by a wireless network operator, a wired network operator, and/or an Internet Service Provider (ISP). For example, an address may comprise a domestic or international telephone number, an Internet Protocol (IP) address, and/or one or more other identifiers. In other embodiments, a computing and/or communications network may be embodied as a wired network, wireless network, or any combinations thereof.

A computing and/or network device may include and/or may execute a variety of now known and/or to be developed operating systems, derivatives and/or versions thereof, including computer operating systems, such as Windows, iOS, Linux, a mobile operating system, such as iOS, Android, Windows Mobile, and/or the like. A computing device and/or network device may include and/or may execute a variety of possible applications, such as a client software application enabling communication with other devices. For example, one or more messages (e.g., content) may be communicated, such as via one or more protocols, now known and/or later to be developed, suitable for communication of email, short message service (SMS), and/or multimedia message service (MMS), including via a network, such as a social network, formed at least in part by a portion of a computing and/or communications network, including, but not limited to, Facebook®, LinkedIn®, Twitter®, Flickr®, and/or Google+®, to provide only a few examples. A computing and/or network device may also include executable computer instructions to process and/or communicate digital content, such as, for example, textual content, digital multimedia content, and/or the like. A computing and/or network device may also include executable computer instructions to perform a variety of possible tasks, such as browsing, searching, playing various forms of digital content, including locally stored and/or streamed video, and/or games such as, but not limited to, fantasy sports leagues. The foregoing is provided merely to illustrate that claimed subject matter is intended to include a wide range of possible features and/or capabilities.

In FIG. 9, computing device 902 may provide one or more sources of executable computer instructions in the form of physical states and/or signals (e.g., stored in memory states), for example. Computing device 902 may communicate with computing device 904 by way of a network connection, such as via network 908, for example. As previously mentioned, a connection, while physical, may not necessarily be tangible. Although computing device 904 of FIG. 9 shows various tangible, physical components, claimed subject matter is not limited to a computing devices having only these tangible components as other implementations and/or embodiments may include alternative arrangements that may comprise additional tangible components or fewer tangible components, for example, that function differently while achieving similar results. Rather, examples are provided merely as illustrations. It is not intended that claimed subject matter be limited in scope to illustrative examples.

Memory 922 may comprise any non-transitory storage mechanism. Memory 922 may comprise, for example, primary memory 924 and secondary memory 926, additional memory circuits, mechanisms, or combinations thereof may be used. Memory 922 may comprise, for example, random access memory, read only memory, non-volatile memory (e.g., NVRAM) etc., such as in the form of one or more storage devices and/or systems, such as, for example, SDRAM, NAND flash, NOR flash, a disk drive including an optical disc drive, a tape drive, a solid-state memory drive, etc., just to name a few examples.

Memory 922 may be utilized to store a program of executable computer instructions. For example, processor 920 may fetch executable instructions from memory and proceed to execute the fetched instructions. Memory 922 may also comprise a memory controller for accessing device readable-medium 940 that may carry and/or make accessible digital content, which may include code, and/or instructions, for example, executable by processor 920 and/or some other device, such as a controller, as one example, capable of executing computer instructions, for example. Under direction of processor 920, a non-transitory memory, such as memory cells storing physical states (e.g., memory states), comprising, for example, a program of executable computer instructions, may be executed by processor 920 and able to generate signals to be communicated via a network, for example, as previously described. Generated signals may also be stored in memory, also previously suggested.

Memory 922 may store electronic files and/or electronic documents, such as relating to one or more users, and may also comprise a computer-readable medium that may carry and/or make accessible content, including code and/or instructions, for example, executable by processor 920 (e.g., central processing unit, graphics processing unit or neural network processing unit, or any combination thereof) and/or some other device, such as a controller, as one example, capable of executing computer instructions, for example. As previously mentioned, the term electronic file and/or the term electronic document are used throughout this document to refer to a set of stored memory states and/or a set of physical signals associated in a manner so as to thereby form an electronic file and/or an electronic document. That is, it is not meant to implicitly reference a particular syntax, format and/or approach used, for example, with respect to a set of associated memory states and/or a set of associated physical signals. It is further noted an association of memory states, for example, may be in a logical sense and not necessarily in a tangible, physical sense. Thus, although signal and/or state components of an electronic file and/or electronic document, are to be associated logically, storage thereof, for example, may reside in one or more different places in a tangible, physical memory, in an embodiment.

Algorithmic descriptions and/or symbolic representations are examples of techniques used by those of ordinary skill in the signal processing and/or related arts to convey the substance of their work to others skilled in the art. An algorithm is, in the context of the present patent application, and generally, is considered to be a self-consistent sequence of operations and/or similar signal processing leading to a desired result. In the context of the present patent application, operations and/or processing involve physical manipulation of physical quantities. Typically, although not necessarily, such quantities may take the form of electrical and/or magnetic signals and/or states capable of being stored, transferred, combined, compared, processed and/or otherwise manipulated, for example, as electronic signals and/or states making up components of various forms of digital content, such as signal measurements, text, images, video, audio, etc.

It has proven convenient at times, principally for reasons of common usage, to refer to such physical signals and/or physical states as bits, values, elements, parameters, symbols, characters, terms, numbers, numerals, measurements, content and/or the like. It should be understood, however, that all of these and/or similar terms are to be associated with appropriate physical quantities and are merely convenient labels. Unless specifically stated otherwise, as apparent from the preceding discussion, it is appreciated that throughout this specification discussions utilizing terms such as "processing," "computing," "calculating," "determining", "establishing", "obtaining", "identifying", "selecting", "generating", and/or the like may refer to actions and/or processes of a specific apparatus, such as a special purpose computer and/or a similar special purpose computing and/or network device. In the context of this specification, therefore, a special purpose computer and/or a similar special purpose computing and/or network device is capable of processing, manipulating and/or transforming signals and/or states, typically in the form of physical electronic and/or magnetic quantities, within memories, registers, and/or other storage devices, processing devices, and/or display devices of the special purpose computer and/or similar special purpose computing and/or network device. In the context of this particular patent application, as mentioned, the term "specific apparatus" therefore includes a general purpose computing and/or network device, such as a general purpose computer, once it is programmed to perform particular functions, such as pursuant to program software instructions.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and/or storage of charge or a release of stored charge. Likewise, in other memory devices, a change of state may comprise a physical change, such as a transformation in magnetic orientation. Likewise, a physical change may comprise a transformation in molecular structure, such as from crystalline form to amorphous form or vice-versa. In still other memory devices, a change in physical state may involve quantum mechanical phenomena, such as, superposition, entanglement, and/or the like, which may involve quantum bits (qubits), for example. The foregoing is not intended to be an exhaustive list of all examples in which a change in state from a binary one to a binary zero or vice-versa in a memory device may comprise a transformation, such as a physical, but non-transitory, transformation. Rather, the foregoing is intended as illustrative examples.

Referring again to FIG. 9, processor 920 may comprise one or more circuits, such as digital circuits, to perform at least a portion of a computing procedure and/or process. By way of example, but not limitation, processor 920 may comprise one or more processors, such as controllers, microprocessors, microcontrollers, application specific integrated circuits, digital signal processors, programmable logic devices, field programmable gate arrays, the like, or any combination thereof. In various implementations and/or embodiments, processor 920 may perform signal processing, typically substantially in accordance with fetched executable computer instructions, such as to manipulate signals and/or states, to construct signals and/or states, etc., with signals and/or states generated in such a manner to be communicated and/or stored in memory, for example.

FIG. 9 also illustrates device 904 as including a component 932 operable with input/output devices, for example, so that signals and/or states may be appropriately communicated between devices, such as device 904 and an input device and/or device 904 and an output device. A user may make use of an input device, such as a computer mouse, stylus, track ball, keyboard, and/or any other similar device capable of receiving user actions and/or motions as input signals. Likewise, for a device having speech to text capability, a user may speak to a device to generate input signals. A user may make use of an output device, such as a display, a printer, etc., and/or any other device capable of providing signals and/or generating stimuli for a user, such as visual stimuli, audio stimuli and/or other similar stimuli.

One particular embodiment described above is directed to a method comprising: generating a first signal to apply a first sensory stimulus to a human subject, the first sensory stimulus to evoke a particular involuntary response by a particular unique individual; generating a second signal to apply a second sensory stimulus to the human subject, the second sensory stimulus being temporally correlated with the first sensory stimulus; inferring that a third signal indicates the particular involuntary response to the first sensory stimulus by the particular unique individual; and authenticating an identity of the human subject as being an identity of the particular unique individual based, at least in part, on a detected temporal correlation of the third signal and a fourth signal indicating an involuntary response to the second sensory stimulus. In one particular implementation, the method further comprises generating the third signal at a sensor positioned on a scalp of the human subject responsive to one or more brain signals generated by the human subject. For example, inferring that the third signal indicates the particular involuntary response to the first sensory stimulus by the particular unique individual may further comprise classifying at least one of the one or more brain signals as a P300 brain signal. In another particular implementation, the second sensory stimulus comprises at least one first frequency characteristic, and wherein the fourth signal comprises a signal generated by a sensor responsive to a steady-state visual evoked potential (SSVEP) signal having at least one second frequency characteristic, the at least one second frequency characteristic being based, at least in part, on the at least one first frequency characteristic. For example, a temporal correlation of the third signal and the fourth signal may be based, at least in part, on temporal correlation of the third signal with the at least one second frequency characteristic and a variation in amplitude in the fourth signal. In another particular implementation, the first and second sensory stimuli comprise images. In another particular implementation, generating the first signal to apply the first sensory stimulus to the human subject further comprises presenting at least one visual image of particular significance to the particular unique individual temporally interleaved with presentation of one or more images which are not of particular significance to the particular user. For example, the at least one visual image of particular significance to the particular unique individual may evoke a P300 brain signal in the particular unique individual. In another particular implementation, the method further comprises determining the temporal correlation of the third signal and the fourth signal based, at least in part, on a difference between a time of detection of a characteristic of the third signal and a time of detection of a characteristic of the fourth signal. In another particular implementation, generating the first signal to apply the sensory stimulus to the human subject further comprises generating at least one sound of particular significance to the particular unique individual temporally interleaved with at least one sound that is not of particular significance to the particular unique individual. In another particular implementation, the first sensory stimulus comprises application of pressure at known locations of the human subject's scalp. In another particular implementation, generating the first signal to apply a first sensory stimulus to the human subject further comprises: fetching an electronic document associated with the identity of the particular unique individual from a non-transitory device-readable memory; and executing device readable instructions by a computing device to generate control and/or content signals based, at least in part, on the fetched electronic document.

Another particular embodiment described above is directed to an apparatus comprising: one or more processors to generate a first signal to apply a first sensory stimulus to a human subject, the first sensory stimulus to evoke a particular involuntary response by a particular unique individual, and to generate a second signal to apply a second sensory stimulus to the human subject, the second sensory stimulus being temporally correlated with the first sensory stimulus; one or more first sensors to generate a third signal responsive to a first involuntary response by the human subject to application of the first sensory stimulus; and one or more second sensors to generate a fourth signal responsive to a second involuntary response by the human subject to application of the second sensory stimulus, wherein the one or more processors are further to: infer that the third signal indicates the particular involuntary response to the first sensory stimulus by the particular unique individual; and authenticate an identity of the human subject as being an identity of the particular unique individual based, at least in part, on a detected temporal correlation of the third signal and a fourth signal indicating an involuntary response to the second sensory stimulus. In one particular implementation, the one or more processors are further to: fetch an electronic document associated with the identity of the particular unique individual from a non-transitory device-readable memory; and execute device readable instructions to generate the first signal as control and/or content signals based, at least in part, on the fetched electronic document. For example, the one or more processors may be further to: determine the detected temporal correlation of the third signal and the fourth signal based, at least in part, on an expected time difference between detection of an event in third signal and detection of an event in the fourth signal, the expected time difference being obtained from the fetched electronic document. In another particular implementation, the one or more processors are further to infer that the third signal indicates the particular involuntary response to the first sensory stimulus by the particular unique individual based, at least in part, on a classification of at least one brain signal generated by the s as a P300 brain signal. In another particular implementation, the second sensory stimulus comprises at least one first frequency characteristic, and wherein the fourth signal comprises a signal generated by a sensor responsive to a steady-state visual evoked potential (SSVEP) signal having at least one second frequency characteristic, the at least one second frequency characteristic being based, at least in part, on the at least one first frequency characteristic. For example, the one or more processors may be further to detect the temporal correlation of the third signal and the fourth signal based, at least in part, on a temporal correlation of the third signal with the at least one second frequency characteristic and a variation in amplitude in the fourth signal.

Another particular embodiment described above is directed to an article comprising: a non-transitory storage medium comprising device-readable instructions stored thereon that are executable by a processor to: generate a first signal to apply a first sensory stimulus to a human subject, the first sensory stimulus to evoke a particular involuntary response by a particular unique individual; generate a second signal to apply a second sensory stimulus to the human subject, the second sensory stimulus being temporally correlated with the first sensory stimulus; infer that a third signal indicates the particular involuntary response to the first sensory stimulus by the particular unique individual; and authenticate an identity of the human subject as being an identity of the particular unique individual based, at least in part, on a detected temporal correlation of the third signal and a fourth signal indicating an involuntary response to the second sensory stimulus.

In the preceding description, various aspects of claimed subject matter have been described. For purposes of explanation, specifics, such as amounts, systems and/or configurations, as examples, were set forth. In other instances, well-known features were omitted and/or simplified so as not to obscure claimed subject matter. While certain features have been illustrated and/or described herein, many modifications, substitutions, changes and/or equivalents will now occur to those skilled in the art. It is, therefore, to be understood that the appended claims are intended to cover all modifications and/or changes as fall within claimed subject matter.

What is claimed is:

1. A method comprising:
    executing one or more first trained neural networks to obtain one or more context features based, at least in part, on first sensor signals generated by one or more first sensors responsive to a physical environment experienced by a subject;
    selecting a response signature from among a plurality of response signatures maintained in a repository of response signatures for a particular unique individual based, at least in part, on an association of at least one of the one or more context features with a repository of context features;
    executing one or more second trained neural networks to obtain one or more involuntary response features determined based, at least in part, on second sensor signals generated by one or more second sensors, the second sensor signals being based, at least in part on or responsive to one or more involuntary responses of the subject to the physical environment;
    electronically authenticating an identity of the subject as being an identity of the particular unique individual based, at least in part, on the one or more context features and the one or more involuntary response features to provide an authentication result; and updating one or more of the plurality of response signatures for the particular unique individual maintained in the repository based, at least in part, on the authentication result and the obtained one or more context features.

2. The method of claim 1, wherein electronically authenticating the identity of the subject as being the identity of the particular unique individual further comprises determining a binary authentication result based, at least in part, on application of a Bayesian detector to the one or more involuntary response features and the one or more context features.

3. The method of claim 1, wherein executing the one or more first trained neural networks to obtain the one or more context features further comprises:

determining a state of the subject as being agitated, ill, rested or tired, or a combination thereof, based, at least in part, on observations of the subject; and determining the one or more context features based, at least in part, on the determined state.

4. The method of claim 1, wherein the one or more context features are further determined based, at least in part, on recognition of one or more objects in one or more images captured by a camera co-located with the subject or recognition of one or more recorded sounds, or a combination thereof.

5. The method of claim 4, wherein the one or more context features are obtained further based, at least in part, on an association of the recognized one or more objects with one or more objects of significance to the particular unique individual.

6. The method of claim 1, wherein the second sensor signals are generated by one or more second sensors responsive, at least in part, to detected or measured eye blinking, detected or measured eye movement, detected or measured pupillary response, MEG scan signal, body temperature, blood pressure, brain signals or perspiration, or a combination thereof, of the subject.

7. The method of claim 1, wherein the second sensor signals are based, at least in part on or responsive to one or more P300 brain signals of the subject or one or more steady-state visual evoked potential (SSVEP) signals of the subject, or a combination thereof.

8. The method of claim 1, wherein the one or more context features are obtained further based, at least in part, on one or more images captured at a camera or signals generated by one or more first sensors.

9. The method of claim 8, wherein the one or more first sensors comprise at least one environmental sensor or at least one inertial sensor, or a combination thereof.

10. The method of claim 1, wherein the one or more context features are further based, at least in part on, or responsive to signals from a camera, one or more environmental sensors, one or more inertial sensors, one or more location determining devices, or a combination thereof.

11. The method of claim 1, wherein the repository of context features are to be maintained in a non-transitory memory, and wherein the method further comprises updating at least a portion of the repository of context features based, at least in part, on at least one of the one or more context features, at least one of the one or more involuntary response features and authentication of the identity of the subject as being the identity of the particular unique individual.

12. The method of claim 1, wherein electronically authenticating the identity of the subject as being the identity of the particular unique individual to be performed at a frequency based, at least in part, on a security level.

13. The method of claim 1, wherein the one or more context features are further based, at least in part, on:

a state of the subject determined by the one or more first trained neural networks.

14. The method of claim 1, wherein:

one or more features of the one or more second trained neural networks are trained based, at least in part, on observations of responses by the particular unique individual to stimuli over time; and the method further comprises determining the response signature based, at least in part, on the trained one or more features of the one or more second trained neural networks.

15. The method of claim 14, wherein the stimuli over time to comprise stimuli to physical environments over time.

16. The method of claim 1, and further comprising determining the one or more involuntary response features further based, at least in part, on an application of a multi-variable probabilistic model to at a first observed involuntary response by the subject to the physical environment and at least a second observed involuntary response by the subject to the physical environment comprising an observed P300 brain signal, eye movement, eye blinking, heart rate, pupillary response, body temperature or blood pressure, or any combination thereof.

17. The method of claim 1, and further comprising substituting the physical environment with application of an artificial stimulus to the subject.

18. The method of claim 1, and further comprising providing a prompt to the subject to enter a password in lieu of authenticating based, at least in part, on the one or more involuntary response features and the response signature.

19. A computing device comprising:

one or more processors to:

execute one or more first trained neural networks to obtain one or more context features based, at least in part, on first sensor signals generated by one or more first sensors responsive to a physical environment to be experienced by a subject;

select a response signature from among a plurality of response signatures maintained in a repository of response signatures to be associated with a particular unique individual based, at least in part, on an association of at least one the one or more context features with a repository of context features;

execute one or more second trained neural networks to obtain one or more involuntary response features to be determined based, at least in part, on second sensor signals to be generated by one or more second sensors, the second sensor signals to be based, at least in part on or responsive to one or more involuntary responses of the subject to the physical environment;

authenticate an identity of the subject to be an identity of the particular unique individual based, at least in part, on the one or more context features and the one or more involuntary response features to provide an authentication result; and update one or more of the plurality of response signatures for the particular unique individual maintained in the repository based, at least in part, on the authentication result and the obtained one or more context features.

\* \* \* \* \*